(12) United States Patent
Segal et al.

(10) Patent No.: US 9,024,069 B2
(45) Date of Patent: May 5, 2015

(54) NONOATE DERIVATIVES AND USES THEREOF

(71) Applicant: Ironwood Pharmaceuticals, Cambridge, MA (US)

(72) Inventors: Jeffrey Segal, Needham, MA (US); Nisha Perez, Boston, MA (US); Timothy Claude Barden, Salem, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/074,829

(22) Filed: Nov. 8, 2013

(65) Prior Publication Data

US 2014/0135295 A1    May 15, 2014

Related U.S. Application Data

(60) Provisional application No. 61/724,471, filed on Nov. 9, 2012.

(51) Int. Cl.
| | |
|---|---|
| *A61K 31/655* | (2006.01) |
| *C07C 245/24* | (2006.01) |
| *C07D 207/50* | (2006.01) |
| *C07C 291/00* | (2006.01) |

(52) U.S. Cl.
CPC ............ *C07D 207/50* (2013.01); *A61K 31/655* (2013.01); *C07C 245/24* (2013.01); *C07C 291/00* (2013.01)

(58) Field of Classification Search
CPC ............................ C07C 245/24; A61K 31/655
USPC .......................... 560/316; 564/301; 514/150
See application file for complete search history.

(56) References Cited

U.S. PATENT DOCUMENTS

2009/0054450 A1* 2/2009 Currie et al. ............. 514/252.19

FOREIGN PATENT DOCUMENTS

EP         2266623    * 12/2010    ............. A61K 47/48

* cited by examiner

*Primary Examiner* — Robert Havlin
(74) *Attorney, Agent, or Firm* — McCarter & English, LLP; Steven G. Davis; Jill Ann Mello

(57) ABSTRACT

A compound of Formula (I):

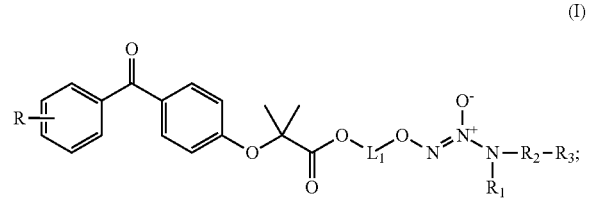

or a pharmaceutically acceptable salt of the compound. Also described are pharmaceutical formulations thereof and methods of using the same.

17 Claims, 8 Drawing Sheets

Figure 1. Fenofibric acid release upon oral dosing of fenofibrate, compound 6, 7, or 8 in male SD rats
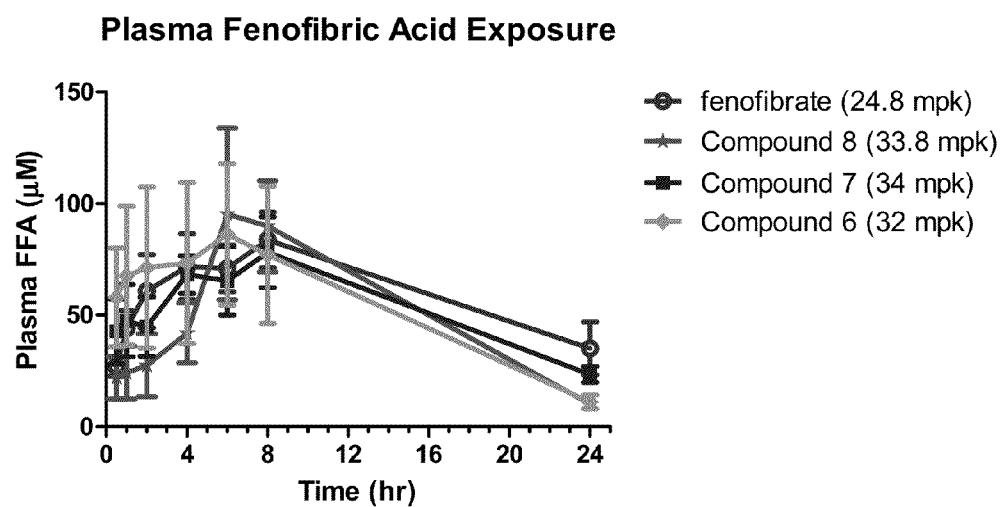

Figure 2. Plasma NO$_x$ levels upon oral dosing of fenofibrate, compound 6, 7, or 8 in male SD rats
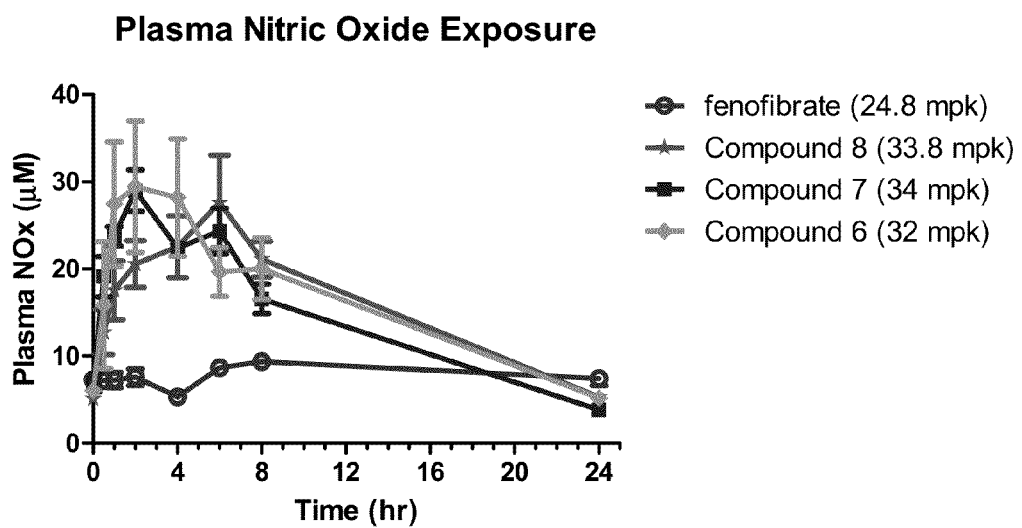

Figure 3. Vasorelaxation upon administration of compounds 6 and 8 to a rat aortic ring preparation.
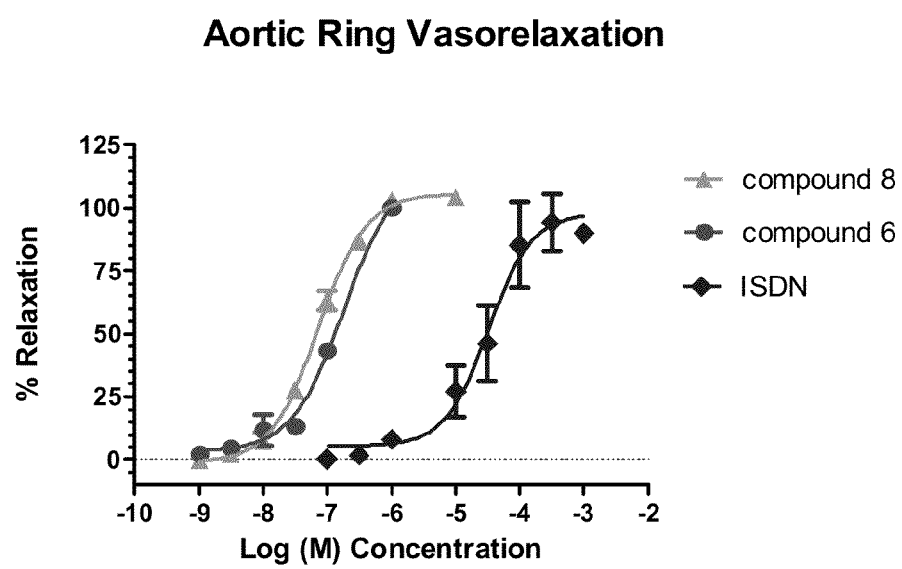

Figure 4. Rat high fat, high cholesterol diet model, VLDL levels from Compound 8 at 3, 10 and 30 mg/kg compared to fenofibrate at 2.2, 7.3 and 22 mg/kg
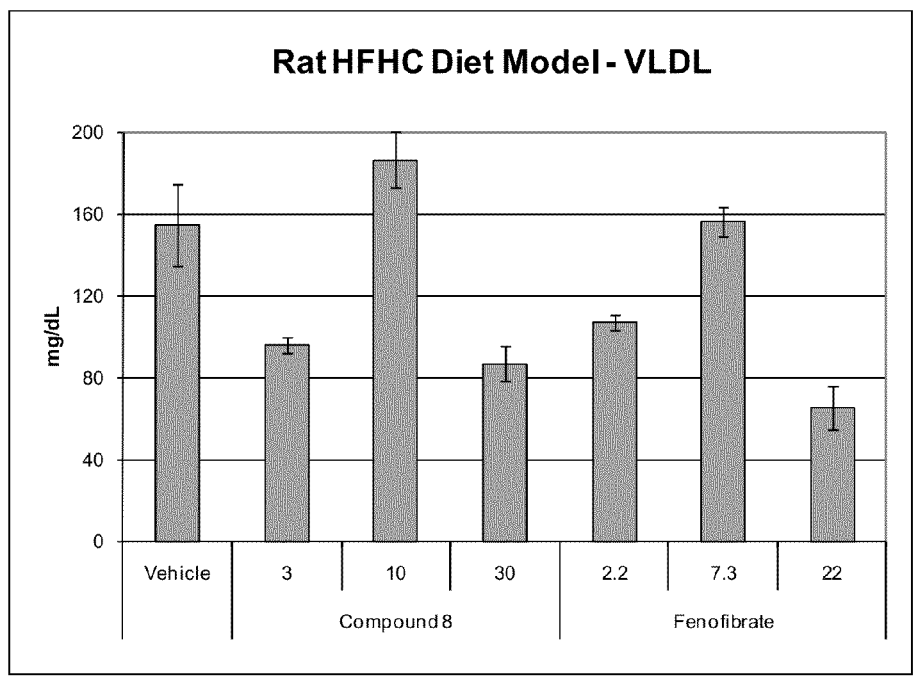

Figure 5. Rat high fat, high cholesterol diet model, HDL levels from Compound 8 at 3, 10 and 30 mg/kg compared to fenofibrate at 2.2, 7.3 and 22 mg/kg
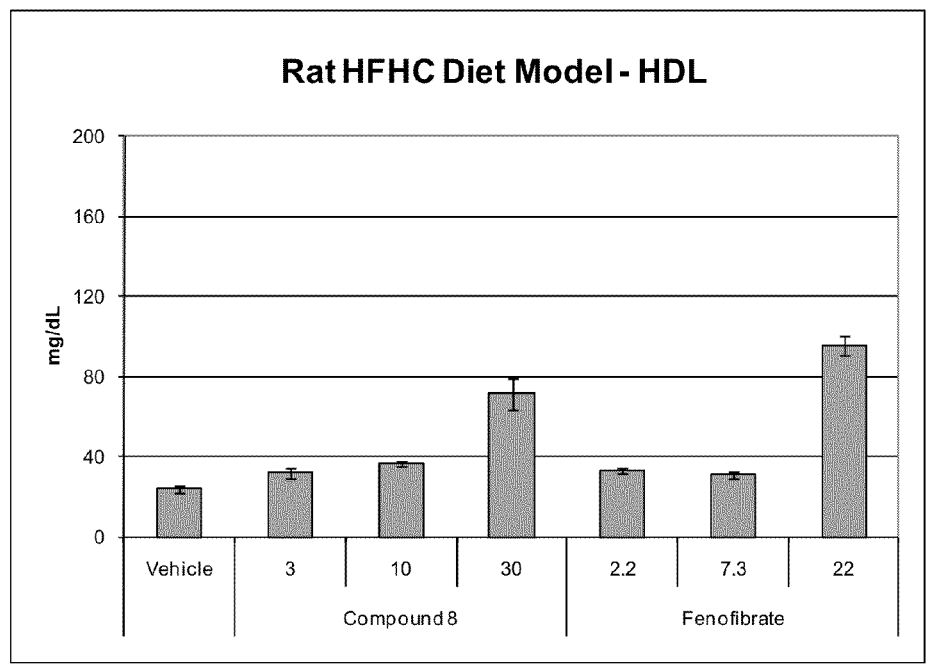

Figure 6. Blood pressure in normotensive rats, Compounds 6, 7, and 8 dosed at 30mg/kg
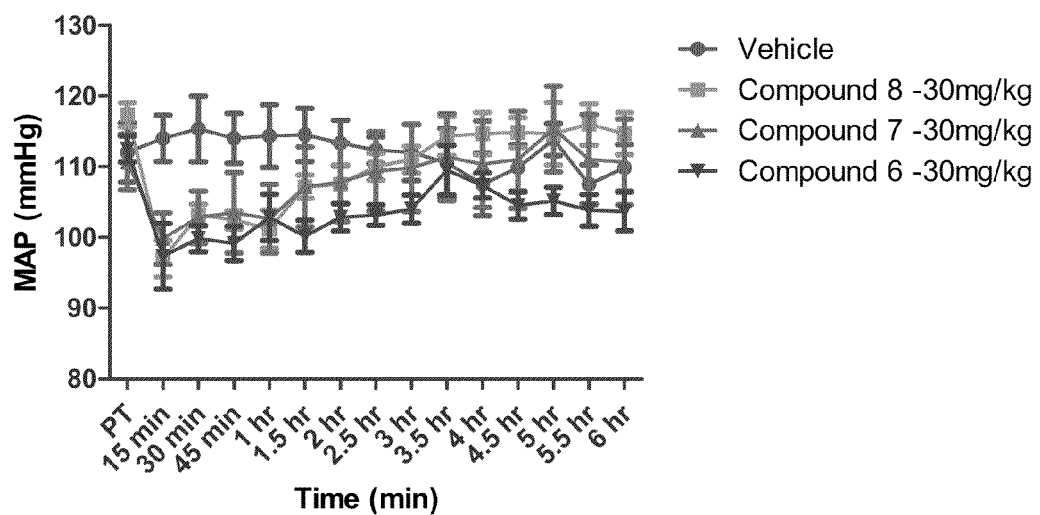

Figure 7. Blood pressure in L-NAME hypertensive rats, Compound 8 dose response
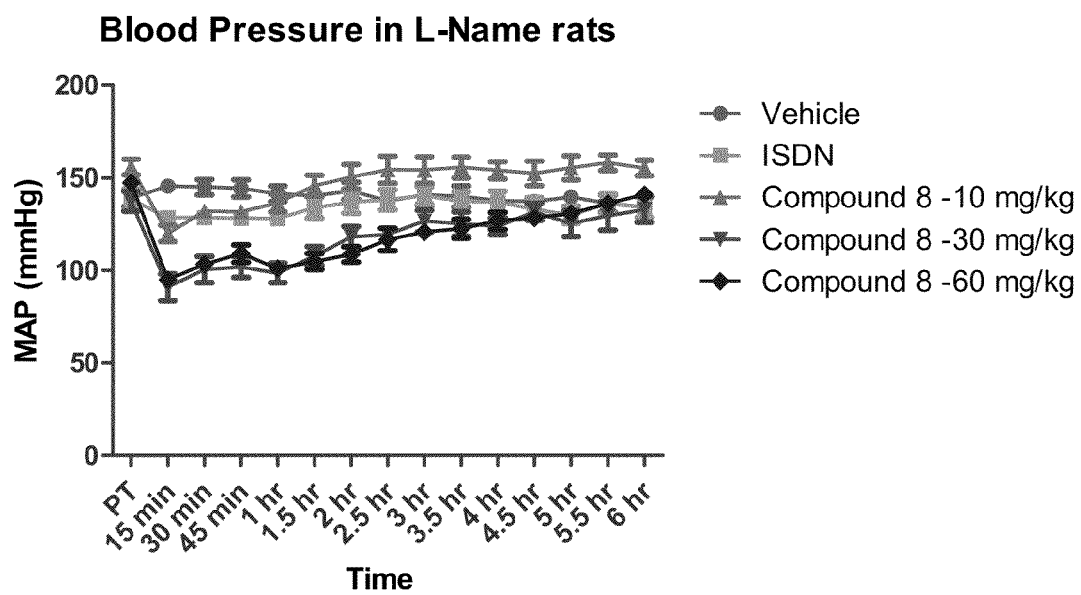

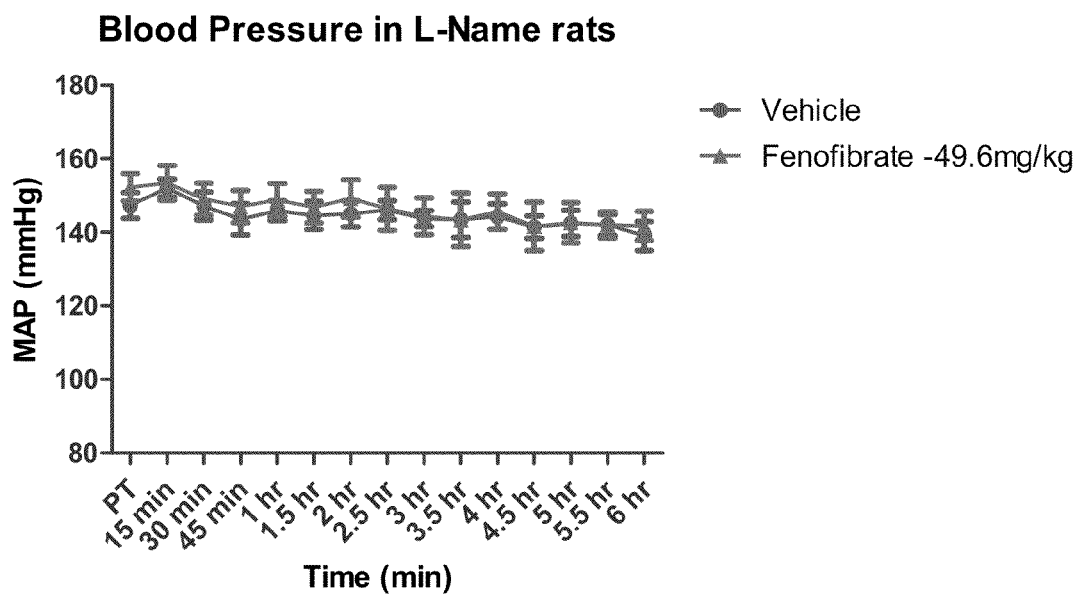
Figure 8. Blood pressure in L-NAME hypertensive rats, fenofibrate dosed at 49.6 mg/kg

NONOATE DERIVATIVES AND USES THEREOF

RELATED APPLICATIONS

This application claims the benefit of U.S. Provisional Application No. 61/724,471, filed Nov. 9, 2012. The entire teachings of the aforementioned application are incorporated herein by reference.

FIELD OF THE INVENTION

The present invention relates to novel NONOate derivatives, and pharmaceutical formulations thereof, used for increasing nitric oxide levels in a subject in need thereof.

BACKGROUND OF THE INVENTION

Nitric oxide (NO) has recently been shown to dramatically reduce thrombocyte and fibrin aggregation/adhesion and smooth muscle cell hyperplasia while promoting endothelial cell growth. NO has also been implicated as part of a cascade of interacting agents involved in a wide variety of bioregulatory processes, including the physiological control of blood pressure, macrophage-induced cytostasis and cytotoxicity, neurotransmission, cancer, and infectious diseases. Given that NO plays a role in such a wide variety of bioregulatory processes, great effort has been expended to develop compounds capable of releasing NO.

Despite the extensive literature available on NO and nitric oxide-releasing compounds, there remains a need for stable nitric oxide-releasing compounds.

SUMMARY OF THE INVENTION

Applicants have now discovered that certain NONOate derivatives are potent nitric oxide releasing compounds. As such, they are potent in increasing NO levels in a subject in need thereof. Based on this discovery, NONOate derivatives, pharmaceutical compositions thereof, and methods of increasing NO levels with the NONOate derivatives are disclosed herein.

One aspect of the present teachings relates to compounds represented by the structure of Formula I:

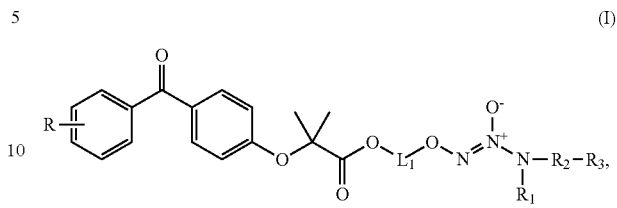

or a pharmaceutically acceptable salt thereof.

R is selected from halogen, —CN, —NO$_2$, C1-C4 alkyl, C1-C4 haloalkyl, C1-C4 alkoxy, C1-C4 haloalkoxy, —C(=O)OR$^a$, and —OC(=O)R$^a$. Alternatively, R is selected from halogen, —CN, C1-C4 alkyl, and C1-C4 haloalkyl;

R$_1$ is H or optionally substituted C1-C4 alkyl;

R$_2$ is optionally substituted C1-C6 alkylene; or

R$_1$ and R$_2$, together with the nitrogen to which they are attached, form a 3-8 membered heterocyclic ring, optionally substituted by R$_3$;

R$_3$ is —H, —OH, —CO$_2$R$^a$, halogen, —NR$^b$R$^c$, —CN, C1-C4 alkyl, C1-C4 haloalkyl, C1-C4 hydroxyalkyl, C1-C4 alkoxy, C1-C4 haloalkoxy, or (C1-C4)alkoxy(C1-C4)alkyl;

L$_1$ is C1-C6 alkylene;

each R$^a$, independently, is —H or C1-C4 alkyl; and

R$^b$ and R$^c$ are each independently selected from —H, C1-C4 alkyl, C1-C4 haloalkyl, hydroxy(C1-C4)alkyl, and (C1-C4)alkoxy(C1-C4)alkyl.

Exemplary compounds of the present teachings are

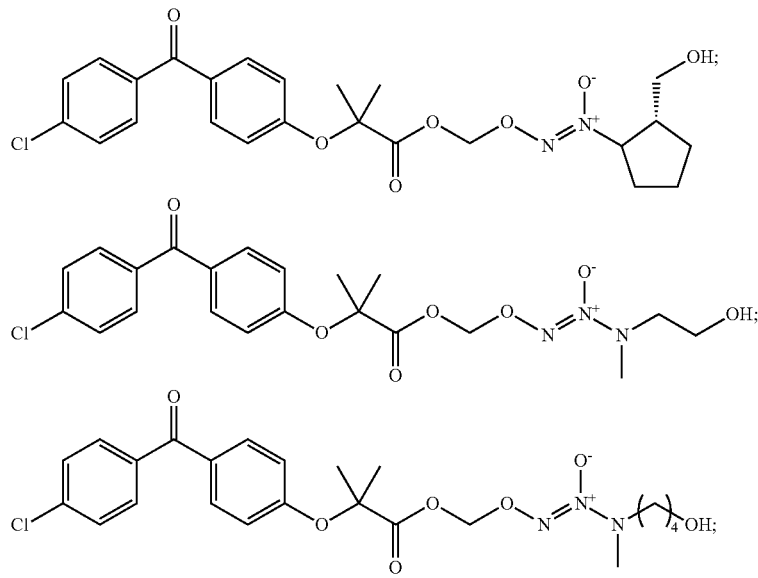

or a pharmaceutically acceptable salt thereof.

Another aspect of the present teachings relates to a pharmaceutical composition comprising a pharmaceutically acceptable carrier or diluent and a compound represented by the structure of formula (I) described above or a pharmaceutically acceptable salt thereof.

Still another aspect of the present teachings relates to a method for increasing NO levels in a subject in need thereof, the method comprising administering to a subject in need thereof a therapeutically effective amount of any of the above-described compounds or compositions.

In one aspect, the subject is in need of treatment for a disease or disorder selected from a lipid related disorder, hypertension, fungal infection, female sexual dysfunction, erectile dysfunction, thrombosis, or inhibiting platelet aggregation in a subject in need thereof.

In another aspect, the subject is in need of treatment for a disease or disorder selected from diabetes, elevated fasting plasma glucose, insulin resistance, elevated glycosylated hemoglobin levels, diabetic retinopathy, proliferative or non-proliferative retinopathy, albuminuria, microalbuminuria, nephropathy, kidney failure, neuropathy, and foot ulcers.

In certain embodiments, the subject may be suffering from (or susceptible to developing) a lipid metabolism disorder including, but not limited to, dyslipidemia, hyperlipidemia, hypercholesterolemia, hypertriglyceridemia, sitosterolemia, familial hypercholesterolemia, primary heterozygous familial hypercholesterolemia, primary non-familial hypercholesterolemia, xanthoma, combined hyperlipidemia, lecithin cholesterol acyltransferase deficiency, tangier disease, abetalipoproteinemia, and fatty liver disease. In certain embodiments, the hypercholesterolemia includes, for example, primary heterozygous familial hypercholesterolemia or primary non-familial hypercho lesterolemia.

In another aspect, the present teachings provide methods for treating and/or preventing a variety of diseases or disorders associated with aging, stress, diabetes, neurodegenerative diseases, obesity, cardiovascular disease, blood clotting disorders, inflammation, and cancer.

Another aspect of the present teachings relates to the use of a compound represented by structure of Formulas (I) or a pharmaceutically acceptable salt thereof for the manufacture of a medicament for increasing NO levels in a subject in need thereof.

Another aspect of the present teachings relates to a compound represented by structure of Formulas (I) or a pharmaceutically acceptable salt thereof for use in increasing NO levels in a subject in need thereof.

BRIEF DESCRIPTION OF THE DRAWINGS

FIG. 1 is a graph showing fenofibric acid PK profile after oral administration of Compounds 6 (32 mg/kg), 7 (34 mg/kg), and 8 (33.8 mg/kg) and Fenofibrate (24.8 mg/kg) in male SD rats.

FIG. 2 is a graph showing $NO_x$ level in the plasma after oral administration of Compounds 6 (32 mg/kg), 7 (34 mg/kg), and 8 (33.8 mg/kg) and Fenofibrate (24.8 mg/kg) in male SD rats.

FIG. 3 is a graph showing vasorelaxation after administration of Compounds 6 and 8 to a rat aortic ring preparation.

FIG. 4 is a graph showing VLDL levels (mg/dL) of high fat, high cholesterol diet rats after administration of Compound 8 (3, 10, and 30 mg/kg) and Fenofibrate (2.2, 7.3, and 22 mg/kg).

FIG. 5 is a graph showing HDL levels (mg/dL) of high fat, high cholesterol diet rats after administration of Compound 8 (3, 10, and 30 mg/kg) and Fenofibrate (2.2, 7.3, and 22 mg/kg).

FIG. 6 is a graph showing blood pressure (mmHg) in normotensive rats after administration of Compounds 6, 7, and 8 at a dose of 30 mg/kg.

FIG. 7 is a graph showing blood pressure (mmHg) in L-NAME hypertensive rats after administration of Compound 8 (10, 30, and 60 mg/kg).

FIG. 8 is a graph showing blood pressure (mmHg) in L-NAME hypertensive rats after administration of Fenofibrate (49.6 mg/kg)

DETAILED DESCRIPTION OF THE INVENTION

In one embodiment, the present teachings are directed to a compound represented by the structure of Formula (I) or a pharmaceutically acceptable salt thereof.

In a first embodiment, the compound is represented by the structure of Formula (II) or (IIa):

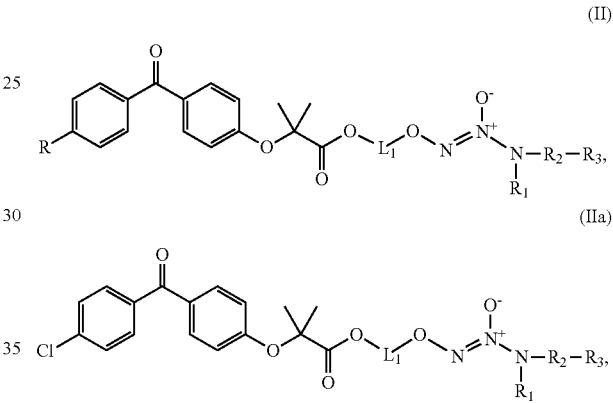

or a pharmaceutically acceptable salt thereof; and values and alternative values for the variables are as described for the structure of Formula (I).

In a second embodiment, for compounds described in structural formula (I), (II), or (IIa), $R_1$ is H or C1-C4 alkyl, optionally substituted with 1 to 3 substituents independently selected from halogen, $-NR^bR^c$, hydroxyl, and C1-C4 alkoxy; and $R_2$ is C1-C6 alkylene, optionally substituted with 1 to 3 substituents independently selected from halogen, $-NR^bR^c$, hydroxyl, and C1-C4 alkoxy; and values and alternative values for the remainder of the variables are as described for the structure of Formula (I).

In a third embodiment, for compounds described in structural formula (I), (II), or (IIa), $R_1$ is H or C1-C4 alkyl; $R_2$ is C1-C6 alkylene; $R_3$ is —H, —OH, C1-C4 hydroxyalkyl, or C1-C4 alkoxy; and $L_1$ is C1-C3 alkylene; and values and alternative values for the remainder of the variables are as described for the structure of Formula (I).

In a fourth embodiment, for compounds described in structural formula (I), (II), or (IIa), $R_1$ is —H or -methyl; $R_3$ is —H, OH, or $CH_2OH$; and $L_1$ is —$CH_2$—; and values and alternative values for the remainder of the variables are as described for the structure of Formula (I) or in the second or third embodiment.

In a fifth embodiment, the compound is represented by the structure of Formula (IIb):

(IIb)

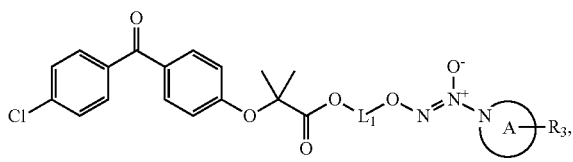

or a pharmaceutically acceptable salt thereof, wherein ring A is a 3-8 membered heterocyclic ring, optionally substituted with a group represented by $R_3$; and values and alternative values for the remainder of the variables are as described for the structure of Formula (I).

In a sixth embodiment, for compounds described in structural formula (I), (II), (IIa), or (IIb), ring A is selected from aziridinyl, diazirinyl, diaziridinyl, azetidinyl, 1,2-diazetidinyl, morpholinyl, thiomorpholinyl, pyrrolidinonyl, pyrrolidinyl, piperidinyl, piperazinyl, hydantoinyl, valerolactamyl, dihydroimidazole, dihydropyridinyl, dihydropyrimidinyl, tetrahydroimidazole, tetrahydropyridinyl, tetrahydropyrimidinyl, azepinyl, diazepinyl, azepanyl, diazepanyl, imidazolyl, isoxazolyl, oxadiazolyl, oxazolyl, pyrazolyl, pyrrolyl, pyridyl, pyrimidinyl, pyridazinyl, thiazolyl, isothiazolyl, triazolyl, and tetrazolyl. Alternatively, ring A is selected from aziridinyl, azetidinyl, pyrrolidinyl, piperidinyl, and morpholinyl; and values and alternative values for the remainder of the variables are as described for the structure of Formula (I).

In a seventh embodiment, for compounds described in structural formula (I), (II), (IIa), or (IIb), ring A is pyrrolidinyl; $R_3$ is —H, —OH, C1-C4 hydroxyalkyl, —$CO_2R^a$, or C1-C4 alkoxy; and $L_1$ is C1-C3 alkylene; and values and alternative values for the remainder of the variables are as described for the structure of Formula (I).

In a eighth embodiment, for compounds described in structural formula (I), (II), or (IIb), $R_3$ is —H, —$CH_2OH$, or —OH and $L_1$ is —$CH_2$—; and values and alternative values for the remainder of the variables are as described for the structure of Formula (I) or in the sixth or seventh embodiment.

The present teachings provide the compounds depicted by structure and/or described by name in the Exemplification, as well as neutral forms and pharmaceutically acceptable salts thereof.

The term "alkyl" used alone or as part of a larger moiety, such as "haloalkyl", "alkoxy", "haloalkoxy", and the like, means saturated aliphatic straight-chain or branched monovalent hydrocarbon radical. Unless otherwise specified, an alkyl group typically has 1-4 carbon atoms, i.e. C1-C4 alkyl. As used herein, a "C1-C4 alkyl" group is means a radical having from 1 to 4 carbon atoms in a linear or branched arrangement.

An "alkylene group" is a saturated aliphatic branched or straight-chain divalent hydrocarbon radical. Unless otherwise specified, an alkylene group typically has 1-6 carbon atoms, i.e. C1-C6 alkylene.

"Alkoxy" means an alkyl radical attached through an oxygen linking atom, represented by —O-alkyl. For example, "(C1-C4)alkoxy" includes methoxy, ethoxy, and propoxy.

The term "hydroxyalkyl" means alkyl substituted with one or more hydroxy groups.

"Alkoxyalkyl" means alkyl substituted with one or more alkoxy groups.

The terms "haloalkyl" and "haloalkoxy" means alkyl or alkoxy, as the case may be, substituted with one or more halogen atoms. The term "halogen" means F, Cl, Br, or I. Preferably the halogen in a haloalkyl or haloalkoxy is F.

A "3-8 membered heterocyclic ring" includes 3-8 membered heterocycloalkyl and 5-8 membered heteroaryl.

"Heterocycloalkyl" means a saturated or unsaturated non-aromatic 3-8 membered ring radical optionally containing one or more double bonds. The heterocycloalkyl contains 1 to 4 heteroatoms, which may be the same or different, selected from N, O or S. The heterocycloalkyl ring optionally contains one or more double bonds. The term "heterocycloalkyl" is intended to include all the possible isomeric forms. Examples of heterocycloalkyl include, but are not limited to, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl.

"Heteroaryl" refers to aromatic ring groups having five to eight ring atoms selected from carbon and at least one (typically 1 to 4, more typically 1 or 2) heteroatoms (e.g., oxygen, nitrogen, or sulfur).

Examples of heteroaryl include, but are not limited to, imidazolyl, isoxazolyl, oxadiazolyl, oxazolyl, pyrazolyl, pyrrolyl, pyridyl, pyrimidinyl, pyridazinyl, thiazolyl, isothiazolyl, triazolyl, and tetrazolyl.

An "optionally substituted heterocyclic ring" is substituted at any one or more substitutable ring atom, which is a ring carbon or ring nitrogen atom bonded to a hydrogen.

Unless otherwise indicated, suitable substituents for an alkyl, alkylene, and heterocyclic group include those substituents which form a stable compound of the invention without significantly adversely affecting the reactivity of the compound of the invention. Examples of substituents for alkyl, alkylene, and heterocyclic include halogen, —CN, —$NO_2$, hydroxyl, C1-C4 alkyl, C1-C4 haloalkyl, C1-C4 alkoxy, C1-C4 haloalkoxy, —C(=O)$OR^a$, —OC(=O)$R^a$, and —$NR^bR^c$, wherein $R^a$ is —H or C1-C4 alkyl; $R^b$ and $R^c$ are each independently selected from —H, C1-C4 alkyl, C1-C4 haloalkyl, hydroxy(C1-C4)alkyl, and (C1-C4)alkoxy (C1-C4)alkyl. In certain embodiments, suitable substituents include halogen, hydroxyl, —$NR^bR^c$, and C1-C4 alkoxy.

The present teachings also include isomers and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers).

Certain of the compounds described herein may exist in various stereoisomeric or tautomeric forms. Stereoisomers are compounds which differ only in their spatial arrangement. The present teachings encompass all such forms, including compounds in the form of essentially pure enantiomers, racemic mixtures and tautomers, which includes forms not depicted structurally. When a disclosed compound is named or depicted by structure without indicating stereochemistry, it is understood that the name or structure encompasses all possible stereoisomers, tautomers, geometric isomers or a combination thereof.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. The present teachings encompass all enantiomerically-pure, enantiomerically-enriched, diastereomerically pure, diastereomerically enriched, and racemic mixtures, and diastereomeric mixtures of the compounds described herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

In one embodiment, the compounds described herein are useful for increasing NO levels in a subject in need thereof. A subject in need of treatment to elevate NO levels includes those with a disease or disorder selected from a lipid related disorder (e.g., hypertension, diabetes, angina, atherosclerosis, and heart failure), impotency (e.g., female sexual dysfunction, erectile dysfunction), fungal infection, thrombosis, or inhibiting platelet aggregation in a subject in need thereof.

A "Lipid related disorder" or "lipid metabolism disorder" includes, for example: reducing blood plasma or serum concentrations of low-density lipoprotein (LDL) cholesterol; reducing concentrations of cholesterol and cholesterol ester in the blood plasma or serum; reducing blood plasma or serum concentrations of apolipoprotein B; reducing blood plasma or serum concentrations of triglycerides; increasing blood plasma or serum concentrations of high density lipoprotein (HDL) cholesterol; increasing fecal excretion of cholesterol; inhibiting the absorption of or reducing plasma or tissue concentration of one or more sterols or stanols; preventing or treating sistoserolemia; preventing or treating vascular diseases/disorders and conditions (including, but not limited to, arteriosclerosis, atherosclerosis, cardiovascular disease, cerebrovascular disease, renovascular disease, mesenteric vascular disease, pulmonary vascular disease, ocular vascular disease and peripheral vascular disease), dyslipidemia, hyperlipidemia (including, but not limited to, hypercholesterolemia, hypertriglyceridemia, sitosterolemia), hypertension, angina, cardiac arrhythmias, congestive heart failure, stroke, and fatty liver disease; reducing the incidence of cardiovascular disease-related events; preventing or treating vascular conditions and associated thrombotic events and blood clotting disorders; preventing or treating inflammation (including, but not limited to, vascular inflammation); reducing blood plasma or serum concentrations of C-reactive protein; preventing, treating, or ameliorating symptoms of Alzheimer's Disease (AD) or other neurodegenerative diseases; regulating production or levels of at least one amyloid β (Aβ) peptide; regulating the amount of ApoE isoform 4 in the bloodstream and/or brain; slowing the aging process and reducing stress-related disorders; preventing or treating obesity; preventing or decreasing the incidence of xanthomas; preventing or minimizing muscular degeneration and related side effects associated with certain HMG-CoA reductase inhibitors (statins); preventing or treating diabetes and associated conditions; preventing or treating at least one autoimmune disorder; preventing or treating demyelination and associated disorders; preventing or treating cancer (including, but not limited to, cholesterol associated tumors); inhibiting the expression of at least one multiple ("multi")-drug resistance gene or protein in an animal cell; enhancing the effectiveness of a chemotherapeutic agent in a subject having cancer; reversing a multi-drug resistance phenotype exhibited by an animal cell; and preventing or treating osteopenia disorders (bone loss disorders).

The present teachings also provide methods for improving lipid parameters in diabetic and non-diabetic patients; improving glycemic control in both Type 2 diabetics and "pre-diabetic" individuals who exhibit elevated fasting plasma glucose and/or insulin resistance; reducing glycosylated hemoglobin levels (HbAic); lowering fasting plasma glucose (FPG) levels; reducing peak and 2-hour post-prandial glucose (PPG) levels; improving insulin sensitivity; reducing insulin resistance; and increasing insulin secretion. The methods are performed by administering to the patient in need thereof a therapeutically effective amount of one or more of the compounds, salts, and/or compositions disclosed herein.

Furthermore, based on rationale that it has been shown that improved glycemic control can reduce the risk of diabetes-associated morbidity and mortality (as demonstrated by the DCCT (Diabetes Control and Complications Trial. Diabetes. 1996 October; 45(10): 1289-98), DCCT/EDIC (Diabetes Control and Complications Trial/Epidemiology of Diabetes Interventions and Complications Trial. Diabetes Care. 1999 January; 22(1):99-111), and UKPPDS (United Kingdom Prospective Diabetes Study. BMJ. 1995 Jan. 14; 310(6972):83-8) trials (amongst others), the compounds, salts, and compositions disclosed herein can be useful for reducing the risk of diabetes-associated complications including, but not limited to: development and progression of diabetic retinopathy; development of proliferative or severe non-proliferative retinopathy; albuminuria; microalbuminuria; nephropathy; kidney failure; cardiovascular disease (including non-fatal myocardial infarction (MI), stroke, or death from CVD); neuropathy; foot ulcers; amputations; hepatic steatosis; steatohepatitis; and cirrhosis.

Hypertension as used herein refers to a physiological state or syndrome in mammals typically characterized by increased peripheral vascular resistance or cardiac output, or both. Clinically, hypertension may optionally be indicated by blood pressure measurements equal to or greater than approximately 140 mm Hg systolic and approximately 90 mm Hg diastolic. Hypertension is further characterized in Oates, "Antihypertensive Agents and the Drug Therapy of Hypertension", Chapter 33, Goodman and Gilman, $9^{th}$ Edition, pages 780. The term used herein includes acute and chronic hypertensive conditions.

Sexual dysfunctions can include, for example, sexual desire disorders, erectile dysfunction, sexual arousal disorders, orgasmic disorders and sexual pain disorders. Female sexual dysfunction (FSD) refers to sexual desire/interest disorders, sexual arousal dysfunctions, women's orgasmic dysfunctions, sexual pain disorders (e.g., dyspareunia and vaginismus), and sexual aversion disorder. The female can be pre-menopausal or menopausal. Sexual dysfunction can be caused, for example, by pregnancy, menopause, cancer, pelvic surgery, chronic medical illness or medications.

FSD occurs in approximately 43% of women ages 18-59 (Frank et al. *Am. Fam. Physician* 2008 (77:5) 635). Female sexual arousal disorder (FSAD) is a category of FSD that accounts for over half of these female sexual complaints. It is characterized by absent/diminished sexual arousal (excitement/pleasure) from sexual stimulation despite genital arousal, or absent/impaired genital sexual arousal from sexual stimulation despite subjective sexual excitement from non-genital stimuli.

Fungal infections treatable with the disclosed compounds include superficial infections and deep tissue, blood, lung and systemic fungal infections. Examples of superficial infections include Athlete's foot (*tinea pedis*), Jock itch (*tinea cruris*), scalp and hair infection (*tinea capitis*), finger or toenail infection (*tinea unguium*), ringworm of the body (*tinea corporis*), skin patches or lesions (*tinea versicolor*), thrush, and candidiadis. Examples of deep tissue, blood, lung and systemic fungal infections include aspergillus, blastomyces, coccidioides, cryptococcus, histoplasma, candida, pneumocystis, mucormycosis.

Thrombosis include, but are not limited to, ischemic stroke, transient ischemic stroke, myocardial infarction, angina pectoris, thrombosis (for example, restenosis, arterial thrombosis, coronary thrombosis, heart valve thrombosis, coronary stenosis, stent thrombosis, graft thrombosis, and first and subsequent thrombotic stroke, and the like), thromboembolism (for example, pulmonary thromboembolism, cerebral thromboembolism, and the like), thrombophlebitis, thrombocytopenia, bleeding disorders, thrombotic occlusion and reocclusion and acute vascular events. Patients who are at risk of developing thromboembolic events, may include those with a familial history of, or genetically predisposed to, thromboembolic disorders, who have had ischemic stroke, transient ischemic stroke, myocardial infarction, and those with unstable angina pectoris or chronic stable angina pectoris and patients with altered prostacyclin/thromboxane $A_2$ homeostasis or higher than normal thromboxane $A_2$ levels leading to increase risk for thromboembolism, including patients with diabetes and rheumatoid arthritis.

Yet another embodiment of the present teachings describes methods for inhibiting platelet aggregation and platelet adhesion. "Platelet adhesion" refers to the contact of a platelet with a foreign surface, including any artificial surface, such as a medical device or instrument, as well as an injured vascular surface, such as collagen. Platelet adhesion does not require platelet activation. Unactivated, circulating platelets will adhere to injured vascular surfaces or artificial surfaces via binding interactions between circulating von Willdebrand factor and platelet surface glycoprotein Ib/IX. "Platelet aggregation" refers to the binding of one or more platelets to each other. Platelet aggregation is commonly referred to in the context of generalized atherosclerosis, not with respect to platelet adhesion on vasculature damaged as a result of physical injury during a medical procedure. Platelet aggregation requires platelet activation which depends on the interaction between the ligand and its specific platelet surface receptor.

Platelet aggregation and platelet adhesion caused by, for example, the exposure of blood to a medical device or instrument by administering to a subject in need thereof a therapeutically effective amount of any of the above-described compounds or compositions.

As used herein, a "therapeutically effective amount" of a drug or pharmaceutical composition or formulation, or agent, described herein is an amount of a drug or agent that, when administered to a subject with a disease or condition, will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

In an embodiment, an effective amount of a compound taught herein ranges from about 0.1 to about 1000 mg/kg body weight, alternatively about 1 to about 500 mg/kg body weight, and in another alternative, from about 20 to about 300 mg/kg body weight. In another embodiment, an effective amount of a compound taught herein ranges from about 0.5 to about 5000 mg/m$^2$, alternatively about from 5 to about 2500 mg/m$^2$, and in another alternative from about 50 to about 1000 mg/m$^2$. The skilled artisan will appreciate that certain factors may influence the dosage required to effectively treat a subject suffering from cancer or reduce the likelihood of recurrence of a cancer. These factors include, but are not limited to, the severity of the disease or disorder, previous treatments, the general health and/or age of the subject and other diseases present.

Moreover, for methods described herein, a "treatment" or dosing regime of a subject with an effective amount of the compound of the present teachings may consist of a single administration, or alternatively comprise a series of applications. For example, the compound of the present teachings may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present teachings, or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required.

As used herein, "treating" or "treatment of" a condition or subject refers to taking steps to obtain beneficial or desired results, including clinical results. Beneficial or desired clinical results can include, but are not limited to, alleviation or amelioration of one or more symptoms or conditions, diminishment of extent of disease, stabilized (i.e. not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

Administration of any of the compounds, compositions, or formulations described in detail herein includes parallel administration (i.e., administration of elements of the formulation to the subject over a period-of time), co-administration or sequential administration (in which elements of the formulation are administered at approximately the same time, e.g., within about a few seconds to a few hours of one another), and simultaneous or co-formulation (in which elements of the formulation are combined or compounded into a single dosage form suitable for oral or parenteral administration).

Combination therapy can be achieved by administering two or more agents, e.g., a compound described herein in combination with one or more agents chosen from lipid altering agents, resveratrol, imidazoline receptor agonists, and PDE inhibitors, each of which is formulated and administered separately, or by administering two or more agents in a single formulation. For example, a compound described herein can be combined with one or more of (1) an amino-containing compound such as, but not limited to, aminoguanidine, agmatine, or amino-tetrazole, (2) resveratrol and (3) an imidazoline receptor agonist such as, but not limited to, LNP509, S-21663, S-22068, or S-23515. This combination can be accomplished by addition of the separate agents or by direct chemical coupling of the agents as disclosed herein to form a single compound. One or more lipid altering agents and/or PDE inhibitors can also be included in the fibric acid/statin/(amino-containing compound/resveratrol/imidazoline receptor agonist) combination. Each of the agents can be formulated and administered separately, or in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

The compounds or compositions described herein can be formulated and administered in combination with "lipid altering agent" or "dyslipidemia agent." The term "lipid altering agent" refers to compounds including, but not limited to, bile acid sequestrants such as cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colesevelam hydrochloride (such as WELCHOL® tablets (polyallylamine hydrochloride) cross-linked with epichlorohydrin and alkylated with 1-bromodecane and (6-bromohexyl)-trimethylammonium bromide) which are available from Sankyo), colestipol (a copolymer of diethylenetriamine and 1-chloro-2,3-epoxypropane, such as COLESTID® tablets which are available from Pharmacia), dialkylaminoalkyl derivatives of a cross-linked dextran, LOCHOLEST®, DEAE-Sephadex (SECHOLEX®, POLICEXIDE®), water soluble derivatives such as 3,3-ioene, N-(cycloalkyl)alkylamines and poliglusam, insoluble quaternized polystyrenes, saponins and mixtures thereof and those bile acid sequestrants disclosed in WO97/11345, WO98/57652, U.S. Pat. Nos. 3,692,895, and 5,703,188. Suitable inorganic cholesterol sequestrants include bismuth salicylate plus montmorillonite clay, aluminum hydroxide and calcium carbonate antacids.

HMG-CoA reductase inhibitors are dyslipidemic agents that can be used in therapeutic combinations with compounds described herein. Suitable HMG-CoA reductase inhibitors for use in therapeutic combination with a compounds described herein include: atorvastatin (LIPITOR®; disclosed in U.S. Pat. Nos. 4,681,893, 5,385,929 and 5,686,104), atorvastatin calcium (disclosed in U.S. Pat. No. 5,273,995), dihydrocompactin, (disclosed in U.S. Pat. No. 4,450,171), bervastatin (disclosed in U.S. Pat. No. 5,082,859), carvastatin, crilvastatin, dalvastatin (disclosed in EP738510A2), fluvastatin (LESCOL®; disclosed in U.S. Pat. Nos. 4,739,073 and 534772), glenvastatin, fluindostatin (disclosed in EP363934A1), velostatin (visinolin; disclosed in U.S. Pat. Nos. 4,448,784 and 4,450,171), lovastatin (mevinolin; MEVACOR® (Merck and Co.) and related compounds disclosed in U.S. Pat. No. 4,231,938), mevastatin (and related compound disclosed in U.S. Pat. No. 3,983,140), compactin (and related compounds disclosed in U.S. Pat. No. 4,804,770), pitavastatin (also known as NK-104, itavastatin, nisvastatin, nisbastatin disclosed in U.S. Pat. No. 5,102,888), pravastatin (PRAVACHOL® (Bristol Myers Squibb) and related compounds disclosed in U.S. Pat. No. 4,346,227), rivastatin (sodium 7-(4-fluorophenyl)-2,6-diisopropyl-5-methoxymethylpyridin-3-yl)-3,5-dihydroxy-6-heptanoate), rosuvastatin (CRESTOR®; also known as ZD-4522 disclosed in U.S. Pat. No. 5,260,440), atavastatin, visastatin, simvastatin (ZOCOR® (Merck and Co.) and related compounds as disclosed in U.S. Pat. No. 4,448,784 and U.S. Pat. No. 4,450,171), simvastatin, CI-981, compounds disclosed in WO03/033481, U.S. Pat. Nos. 4,231,938, 4,444,784, 4,647, 576, 4,686,237, 4,499,289, 4,346,227, 5,753,675, 4,613,610, EP0221025, and EP491226, and optical or geometric isomers thereof; and nontoxic pharmaceutically acceptable salts, N-oxides, esters, quaternary ammonium salts, and prodrugs thereof. In HMG-CoA reductase inhibitors where an open-acid form can exist, salt and ester forms may preferably be formed from the open-acid, and all such forms are included within the meaning of the term "HMG-CoA reductase inhibitor" as used herein. Pharmaceutically acceptable salts with respect to the HMG-CoA reductase inhibitor includes non-toxic salts of the compounds which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzim-idazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamoate, palmitate, panthothenate, phosphate/diphosphate, polygalacturonate, salicylate, stearate, subacetate, succinate, tannate, tartrate, teoclate, tosylate, triethiodide, and valerate.

Soluble guanylate cyclase modulators are dyslipidemic agents that can be used in therapeutic combinations with compounds described herein. Soluble guanylate cyclase (sGC) is a nitric oxide (NO) sensing haemprotein that has been described in many eukaryotes. In response to various stimuli sGC converts GTP into the $2^{nd}$ messenger cyclic cGMP. GC is a heterodimeric protein consisting of homologous alpha and beta subunits. Each consists of an N-terminal domain which may bind haem-nitric oxide and/or oxygen, a central domain of unknown function, and a C-terminal consensus nucleotide cyclase domain. sGC can be activated via both nitric oxide (NO) dependent and independent manners. When NO binds to the haem prosthetic group in the beta subunit of sGC, catalysis is accelerated by 2-3 orders of magnitude. Agents that function as sGC modulators include but are not limited to: NO donors, eNOS transcriptional enhancers, haem-dependent sGC stimulators, haem-independent sGC activators and NOS substrates.

NO Donors

NO donors are pharmacologically active substances that release NO in vivo or in vitro. There are different classes of NO donors, which include organic nitrates, e.g., nitroglycerin, isosorbides (e.g. isosorbide dinitrate, isosorbide mononitrate, isosorbide 5-mononitrate, isosorbide 2-mononitrate, CA Registry no. 16051-77-7), S-nitrosothiols, iron-nitrosyl complexes {e.g., sodium nitroprusside), sydnonimines, C-nitroso compounds, and secondary amine/NO complex ions.

Specific examples of some of the classes of NO donors named above include: Isosorbide (Dilatrate®-SR, Imdur®, Ismo®, Isordil®, Isordil® Titradose®, Monoket®), FK 409 (NOR-3); FR 144420 (NOR-4); 3-morpholinosydnonimine; Linsidomine chlorohydrate ("SIN-I"); S-nitroso-N-acetylpenicillamine ("SNAP"); AZD3582 (CINOD lead compound), NCX 4016, NCX 701, NCX 1022, HCT 1026, NCX 1015, NCX 950, NCX 1000, NCX 1020, AZD 4717, NCX 1510/NCX 1512, NCX 2216, and NCX 4040 (all available fromNicOx S.A.), S-nitrosoglutathione (GSNO), S-nitrosoglutathione mono-ethyl-ester (GSNO-ester), 6-(2-hydroxy-1-methyl-1-nitrosohydrazino)-N-methyl-1-hexanamine (NOC-9) or diethylamine NONOate, S-nitrosothiol, a nitrite, a sydnonimine, a NONOate, a N-nitrosoamine, a N-hydroxyl nitrosamine, a nitrosimine, a diazetine dioxide, an oxatriazole 5-imine, an oxime, a hydroxylamine, a N-hydroxyguanidine, a hydroxyurea or a furoxan. Nitric oxide donors are also as disclosed in U.S. Pat. Nos. 5,155,137; 5,366,997; 5,405,919; 5,650,442; 5,700,830; 5,632,981; 6,290,981; 5,691,423; 5,721,365; 5,714,511; 6,511,911; and 5,814,666, Chrysselis et al. (2002) J Med Chem. 45:5406-9 (such as NO donors 14 and 17), and Nitric Oxide Donors for Pharmaceutical and Biological Research, Eds: Peng George Wang, Tingwei Bill Cai, Naoyuki Taniguchi, Wiley, 2005.

NO donors have a nitrate functionality within the molecule, and a nitroso functional group is present in all of these compounds. Glyceryl trinitrate (also known as GTN, nitroglycerin, nitroglycerine, and trinitrogylcerin) is the nitrate ester of glycerol. In sodium nitroprusside (SNP) a molecule of nitric oxide is coordinated to iron metal forming the square bipyramidal complex. 3-Morpholinosydnonimine (SIN-I) is a zwitterionic compound formed by combination of a morpholine and a sydnonimine. S-nitroso-N-acetylpenicillamine (SNAP) is an N-acetylated amino acid derivative with a nitrosothiol functional group. Diethylenetriamine/NO (DETA/NO) is a compound of nitric oxide covalently linked to diethylenetriamine. NCX 4016 is an m-nitroxymethyl phenyl ester of acetyl salicyclic acid.

The amount and duration of NO release by the respective NO donors determines their pharmacological properties. In vivo, some compounds act rapidly, and the amount of NO released is relatively small. In others, such as NCX 4016 (NO aspirin), the effect is slow and lasts for hours. The route of administration (oral and parenteral) and the duration of release of NO also differ. NO is connected with a specific molecular target; by binding to iron in the haem group of sGC, it produces cyclic guanosine monophosphate (cGMP), which activates a cascade of cellular processes.

The classic nitrovasodilators, organic nitrate and nitrite esters, including nitroglycerin, amyl nitrite, isosorbide dinitrate, isosorbide 5-mononitrate, and nicorandil, have been used for many years in the treatment of cardiovascular diseases. Their principal action is vasorelaxation/vasodilation, mediated by guanylyl cyclase activation and by direct inhibition of nonspecific cation channels in vascular smooth muscle cells (VSMCs). As such, these agents represent the prototypical form of NO-replacement therapy. All of the organic nitrate esters are prodrugs requiring enzymatic metabolism to generate bioactive NO. The major enzyme system involved is located within microsomal membranes, has an estimated apparent molecular mass of 160 kDa, and manifests enhanced activity in the presence of reducing equivalents, especially thiols, which potentiate the action of organic nitrate esters. Although the enzyme has not been more specifically characterized, growing evidence suggests that the cytochrome P-450 system, in conjunction with NADPH and glutathionestransferase activities, is required for the linked metabolic processes of denitration and reduction of organic nitrate esters to authentic NO.

eNOS Transcriptional Enhancers

Endothelial NO synthase is subject to physiological and pathophysiological regulation both at the transcriptional and at the post-transcriptional level. Compounds which enhance eNOS transcription are described in WO 02/064146, WO 02/064545, WO 02/064546 and WO 02/064565, and corresponding patent documents such as US2003/0008915, US2003/0022935, US2003/0022939 and US2003/0055093 for example. Other eNOS transcriptional enhancers include those described in US20050101599 (e.g. 2,2-difluorobenzo[1,3]dioxol-5-carboxylic acid indan-2-ylamide, and 4-fluoro-N-(indan-2-yl)-benzamide), and Sanofi-Aventis compounds AVE3085 and AVE9488 (CA Registry NO. 916514-70-0; Schafer et al, Journal of Thrombosis and Haemostasis 2005; Volume 3, Supplement 1: abstract number P1487).

Haem-dependent sGC Stimulators

Evgenov et al. (2006) Nature Reviews-Drug Discovery 5:755-768 review a novel class of haem-dependent sGC-stimulators which share several characteristics including crucial dependency on the presence of the reduced prosthetic haem moiety and strong synergistic enzyme activation when combined with NO. Haem-dependent sGC stimulators include but are not limited to:

YC-1 (see patent publications EP667345 and DE 19744026)

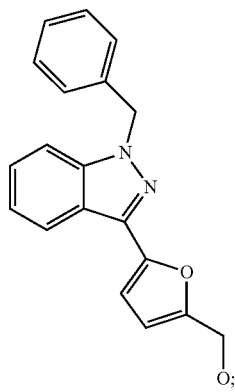

BAY 41-2272 (see patent publications DE 19834047 and DE 19942809)

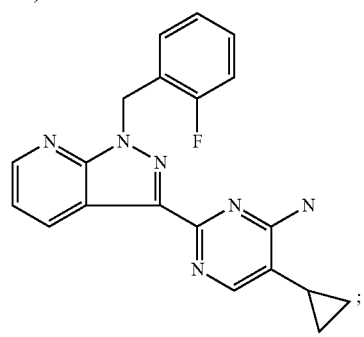

BAY 41-8543 (see patent publication DE 19834044)

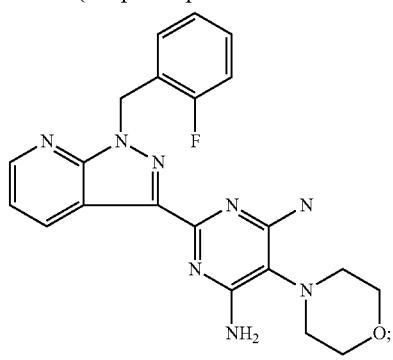

CFM-1571 (see patent publication WO2000027394)

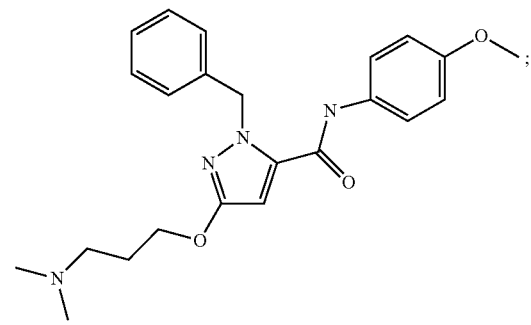

and

A350-619

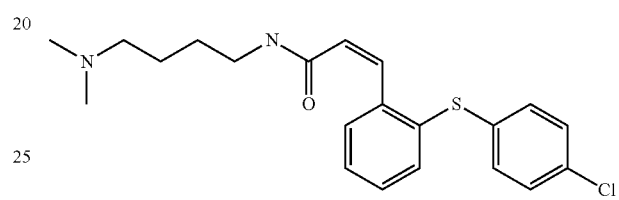

and other compounds disclosed in Tetrahedron Letters (2003), 44(48): 8661-8663.

Haem-independent sGC Activators sGC can also be activated in a NO— and haem-independent manner by haem-independent sGC activators which include but are not limited to:

BAY 58-2667 (see patent publication DE19943635)

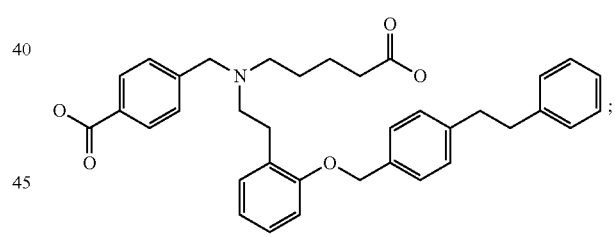

HMR-1766 (ataciguat sodium, see patent publication WO2000002851)

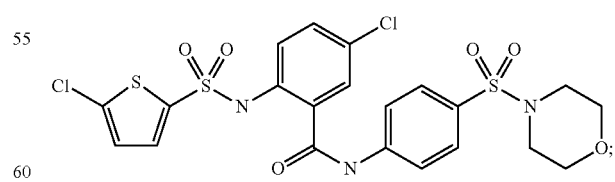

S 3448 (2-(4-chloro-phenylsulfonylamino)-4,5-dimethoxy-N-(4-(thiomorpholine-4-sulfonyl)-phenyl)-benzamide; see patent publications DE19830430 and WO2000002851)

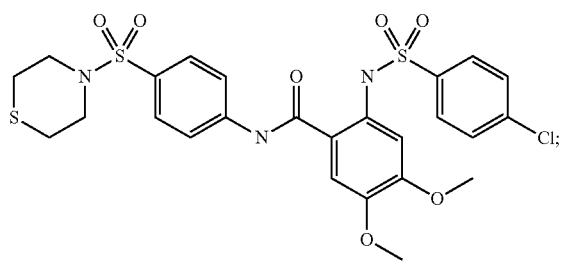 [SMILES: COc1cc(NS(=O)(=O)c2ccc(Cl)cc2)c(C(=O)Nc2ccc(S(=O)(=O)N3CCSCC3)cc2)cc1OC]

and
+
HMR-1069 (Sanofi-Aventis).

NOS Substrates

L-arginine acts as the endogenous substrate of NOS. Other NOS substrates which can be converted to NO may also be useful in the methods described herein. NOS substrates in addition to L-arginine include n-hydroxyguanidine based analogs (such as N[G]-hydroxy-L-arginine (NOHA), (1-(3, 4-dimethoxy-2-chlorobenzylideneamino)-3-hydroxyguanidine), and PR5 (1-(3,4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-caproic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluormethyl) propylguanidine; and others reviewed in Cali et al. (2005) Current Topics in Medicinal Chemistry 5:721-736) and disclosed in the references cited therein.

Other dyslipidemic agents (e.g. lipid altering agents) which can be used in therapeutic combination with a compound described herein include:

HMG-CoA synthase inhibitors such as L-659,699 ((E,E)-11-[3'R-(hydroxy-methyl)-4'-oxo-2'R-oxetanyl]-3,5,7R-trimethyl-2,4-undecadienoic acid) and those disclosed in U.S. Pat. No. 5,120,729, U.S. Pat. No. 5,064,856, and U.S. Pat. No. 4,847,271;

cholesterol absorption inhibitors such as plant sterols, plant stanols and/or fatty acid esters of plant stanols such as sitostanol ester used in BENECOL® margarine, stanol esters, beta-sitosterol, and sterol glycosides such as tiqueside. Other cholesterol absorption inhibitors include 1,4-Diphenylazetidin-2-ones; 4-biarylyl-1-phenylazetidin-2-ones; 4-(hydroxyphenyl)azetidin-2-ones; 1,4-diphenyl-3-hydroxyalkyl-2-azetidinones; A-biphenyl-1-phenylazetidin-2-ones; 4-biarylyl-1-phenylazetidin-2-ones; and A-biphenylylazetidinones;

acyl coenzyme A-cholesterol acyl transferase (ACAT) inhibitors such as avasimibe (Current Opinion in Investigational Drugs. 3(9):291-297 (2003)), eflucimibe, HL-004, lecimibe, DuP-128, KY505, SMP 797, CL-277,082 (Clin Pharmacol Ther. 48(2):189-94 (1990)) and the like; and those disclosed in U.S. Pat. No. 5,510,379, WO96/26948 and WO96/10559;

CETP inhibitors such as JTT 705 identified as in Nature 406, (6792):203-7 (2000), CP 532,632, BAY63-2149, SC 591, SC 795, and the like including those described in Current Opinion in Investigational Drugs. 4(3):291-297 (2003) and those disclosed in J. Antibiot., 49(8): 815-816 (1996), and Bioorg. Med. Chem. Lett., 6:1951-1954 (1996) and patent publications U.S. Pat. No. 5,512,548, U.S. Pat. No. 6,147, 090, WO99/20302, WO99/14204, WO99/41237, WO95/ 04755, WO96/15141, WO96/05227, W0038721, EP796846, EP818197, EP818448, DE19704244, DE19741051, DE19741399, DE197042437, DE19709125, DE19627430, DE19832159, DE19741400, JP 11049743, and JP 09059155;

squalene synthetase inhibitors such as squalestatin-1, TAK-475, and those disclosed in U.S. Pat. Nos. 4,871,721, 4,924,024, 5,712,396 (α-phosphono-sulfonates), Biller et al (1988) J. Med. Chem., 31:1869 (e.g. isoprenoid (phosphinylmethyl)phosphonates), Biller et al (1996) Current Pharmaceutical Design, 2:1, P. Ortiz de Montellano et al (1977) J. Med. Chem. 20:243 (terpenoid pyrophosphates), Corey and Volante (1976) J. Am. Chem. Soc, 98:1291 (farnesyl diphosphate analog A and presqualene pyrophosphate (PSQ-PP) analogs), McClard et al (1987) J.A.C.S., 109:5544 (phosphinylphosphonates), Capson, T. L., PhD dissertation, June, 1987, Dept. Med. Chem. U of Utah, Abstract, Table of Contents, pp 16, 17, 40-43, 48-51, Summary, (cyclopropanes), Curr. Op. Ther. Patents (1993) 861, and patent publications EP0567026A1, EP0645378A1, EP0645377A1, EP0611749A1, EP0705607A2, EP0701725A1, and WO96/ 09827;

antioxidants such as probucol (and related compounds disclosed in U.S. Pat. No. 3,674,836), probucol derivatives such as AGI-1067 (and other derivatives disclosed in U.S. Pat. No. 6,121,319 and U.S. Pat. No. 6,147,250), tocopherol, ascorbic acid, β-carotene, selenium and vitamins such as vitamin B6 or vitamin B 12 and pharmaceutically acceptable salts and esters thereof;

PPARα agonists such as those disclosed in U.S. Pat. No. 6,028,109 (fluorophenyl compounds), WO00/75103 (substituted phenylpropionic compounds), WO98/43081 and fibric acid derivatives (fibrates) such as beclofibrate, benzafibrate, bezafibrate (C.A.S. Registry No. 41859-67-0, see U.S. Pat. No. 3,781,328), binifibrate (C.A.S. Registry No. 69047-39-8, see BE884722), ciprofibrate (C.A.S. Registry No. 52214-84-3, see U.S. Pat. No. 3,948,973), clinofibrate (C.A.S. Registry No. 30299-08-2, see U.S. Pat. No. 3,716,583), clofibrate (such as ethyl 2-(p-chlorophenoxy)-2-methyl-propionate, e.g. Atromid-S® capsules (Wyeth-Ayerst), etofibrate, fenofibrate (such as Tricor® micronized fenofibrate ((2-[4-(4-chlorobenzoyl)phenoxy]-2-methyl-propanoic acid, 1-methylethyl ester; Abbott Laboratories) or Lipanthyl® micronized fenofibrate (Labortoire Founier, France)), gemcabene, gemfibrozil (such as 5-(2,5-dimethylphenoxy)-2,2-dimethylpentanoic acid, e.g. Lopid® tablets (Parke Davis)), lifibrol, GW 7647, BM 170744, LY518674 and those fibrate and fibrate acid derivatives disclosed in WO03/033456, WO03/033481, WO03/043997, WO03/048116, WO03/053974, WO03/ 059864, and WO03/05875;

FXR receptor modulators such as GW 4064, SR 103912, and the like;

LXR receptor modulators such as GW 3965, T9013137, and XTC0179628, and those disclosed in US20030125357, WO03/045382, WO03/053352, WO03/059874, and the like;

thyroid receptor agonists, such as QRX-401 and QRX-431 (QuatRx), GC-24 (described in US 20040110154), KB-2611 and KB-2115 (KaroBioBMS), and those disclosed in WO02/ 15845, WO97/21993, WO99/00353, GB98/284425, U.S. Provisional Application No. 60/183,223, and Japanese Patent Application No. JP 2000256190;

antisense inhibitors of apoB-100 or C reactive protein including, for example, ISIS 301012 and ISIS 353512 (ISIS Pharmaceuticals);

HM74 and HM74A (human HM74A is Genbank Accession No. AY148884 and rat HM74A is EMM_patAR098624)

receptor agonists such as nicotinic acid (niacin) and derivatives thereof (e.g. compounds comprising a pyridine-3-carboxylate structure or a pyrazine-2-carboxylate structure, including acid forms, salts, esters, zwitterions and tautomers, where available) including but not limited to those disclosed in Wise et al (2003) J. Biol. Chem. 278: 9869 (e.g. S-methylpyrazole-S-carboxylic acid and acifran (4,5-dihydro-5-methyl-4-oxo-5-phenyl-2-furan carboxylic acid pyradine-3-acetic acid)), as well as 5-methyl nicotinic acid, nicotinuric acid, niceritrol, nicofuranose, acipimox (5-methylpyrazine-2-carboxylic acid 4-oxide), Niaspan® (niacin extended-release tablets; Kos) and those which can be easily identified by one skilled in the art which bind to and agonize the HM74A or HM74 receptor (for example using the assays disclosed in Wise et al (2003) J. Biol. Chem 278:9869 (nicotine binding and [35S]-GTPγS binding assays), Soga et al (2003) Biochem. Biophys. Res. Comm. 303:364 (radio label binding assay using the HM74 receptor which could be adapted to the HM74A receptor), Tunaru et al (2003) Nature Medicine 9:352 (calcium mobilization assay using the HM74 receptor which could be adapted to the HM74A receptor) and U.S. Pat. No. 6,420,183 (FLIPR assays are described generally in and may be adapted to the HM74A or HM74 receptor);

renin angiotensin system inhibitors;

bile acid reabsorption inhibitors (bile acid reuptake inhibitors), such as BARI 1453, SC435, PHA384640, 58921, AZD7706, and the like;

PPARδ agonists (including partial agonists) such as GW 501516, and GW 590735, and those disclosed in U.S. Pat. No. 5,859,051 (acetophenols), WO03/024395, WO97/28149, WO01/79197, WO02/14291, WO02/46154, WO02/46176, WO02/076957, WO03/016291, WO03/033493, WO99/20275 (quinoline phenyl compounds), WO99/38845 (aryl compounds), WO00/63161 (1,4-disubstituted phenyl compounds), WO01/00579 (aryl compounds), WO01/12612 & WO01/12187 (benzoic acid compounds), and WO97/31907 (substituted 4-hydroxy-phenylalconic acid compound);

sterol biosynthesis inhibitors such as DMP-565;

triglyceride synthesis inhibitors;

microsomal triglyceride transport (MTTP) inhibitors, such as inplitapide, LAB687, and CP346086, AEGR 733, implitapide and the like;

HMG-CoA reductase gene expression inhibitors (e.g. compounds that decrease HMG-CoA reductase expression by affecting (e.g. blocking) transcription or translation of HMG-CoA reductase into protein or compounds that may be biotransformed into compounds that have the aforementioned attributes by one or more enzymes in the cholesterol biosynthetic cascade or may lead to the accumulation of an isoprene metabolite that has the aforementioned activities (such regulation is readily determined by those skilled in the art according to standard assays (Methods of Enzymology, 110:9-19 1985))) such as those disclosed in U.S. Pat. No. 5,041,432 (certain 15-substituted lanosterol derivatives) and E. I. Mercer (1993) Prog. Lip. Res. 32:357 (oxygenated sterols that suppress the biosynthesis of HMG-CoA reductase);

squalene epoxidase inhibitors such as NB-598 ((E)-N-ethyl-N-(6,6-dimethyl-2-hepten-4-y-nyl)-3-[(3,3'-bithiophen-5-yl)methoxy]benzene-methanamine hydrochloride); low density lipoprotein (LDL) receptor inducers such as HOE-402 (an imidazolidinyl-pyrimidine derivative that directly stimulates LDL receptor activity, see Huettinger et al (1993) Arterioscler. Thromb. 13:1005);

platelet aggregation inhibitors;

5-LO or FLAP inhibitors;

PPAR modulators (including compounds that may have multiple functionality for activating various combinations of PPARα, PPARγ, and PPARδ) such as those disclosed in U.S. Pat. Nos. 6,008,237, 6,248,781, 6,166,049, WO00/12491, WO00/218355, WO00/23415, WO00/23416, WO00/23425, WO00/23442, WO00/23445, WO00/23451, WO00/236331, WO00/236332, WO00/238553, WO00/50392, WO00/53563, WO00/63153, WO00/63190, WO00/63196, WO00/63209, WO00/78312, WO00/78313, WO01/04351, WO01/14349, WO01/14350, WO01/16120, WO01/17994, WO01/21181, WO01/21578, WO01/25181, WO01/25225, WO01/25226, WO01/40192, WO01/79150, WO02/081428, WO02/100403, WO02/102780, WO02/79162, WO03/016265, WO03/033453, WO03/042194, WO03/043997, WO03/066581, WO97/25042, WO99/07357, WO99/11255, WO99/12534, WO99/15520, WO99/46232, and WO98/05331 (including GW2331 or (2-(4-[difluorophenyl]-1 heptylureido) ethyl]phenoxy)-2-methylbutyric));

niacin-bound chromium, as disclosed in WO03/039535;

substituted acid derivatives disclosed in WO03/040114;

apolipoprotein B inhibitors such as those disclosed in WO02/090347, WO02/28835, WO03/045921, WO03/047575;

Factor Xa modulators such as those disclosed in WO03/047517, WO03/047520, WO03/048081;

ileal bile acid transport ("IBAT") inhibitors (or apical sodium co-dependent bile acid transport ("ASBT") inhibitors) such as benzothiepines (including 1,2-benzothiazepines; 1,4-benzothiazepines; 1,5-benzothiazepines; 1,2,5-benzothiadiazepines);

PPARδ activators such as disclosed in WO01/00603 (thiazole and oxazole derivates (e.g. C.A.S. Registry No. 317318-32-4), WO97/28149 (fluoro, chloro and thio phenoxy phenylacetic), U.S. Pat. No. 5,093,365 (non-1-oxidizable fatty acid analogues), and WO99/04815. Tests showing the efficacy of the therapy and the rationale for the combination therapy with a dyslipidemic agent are presented in US20030069221 (where the dyslipidemic agents are called 'cardiovascular agents').

The compounds described herein can be used in therapeutic combination with one or more anti-diabetic agents, including but not limited to:

PPARγ agonists such as glitazones (e.g., balaglitazone, ciglitazone, darglitazone (CP-86325, Pfizer), englitazone (CP-68722, Pfizer), isaglitazone (MIT/J&J), MCC-555 (Mitsibishi disclosed in U.S. Pat. No. 5,594,016), pioglitazone (such as such as Actos™ pioglitazone; Takeda), rosiglitazone (Avandia™; Smith Kline Beecham), rosiglitazone maleate, troglitazone (Rezulin®, disclosed in U.S. Pat. No. 4,572,912), GL-262570 (Glaxo Welcome), BRL49653 (disclosed in WO98/05331), CLX-0921, 5-BTZD, GW-0207, LG-100641, JJT-501 (JPNT/P&U), L-895645 (Merck), R-119702 (Sankyo/Pfizer), NN-2344 (Dr. Reddy/NN), YM-440 (Yamanouchi), LY-300512, LY-519818, R483 (Roche), T131 (Tularik), and the like and compounds disclosed in U.S. Pat. No. 5,994,554, WO97/10813, WO97/27857, WO97/28115, WO97/28137, WO97/27847, WO00/76488, WO03/000685, WO03/027112, WO03/035602, WO03/048130, WO03/055867, and pharmaceutically acceptable salts thereof;

biguanides such as metformin hydrochloride ($N_5N$-dimethylimidodicarbonimidic diamide hydrochloride, such as Glucophage™, Bristol-Myers Squibb); metformin hydrochloride with glyburide, such as Glucovance™, Bristol-Myers Squibb); buformin (Imidodicarbonimidic diamide, N-butyl-); etoformine (1-Butyl-2-ethylbiguanide, Schering A.G.) and phenformin;

protein tyrosine phosphatase-IB (PTP-IB) inhibitors, such as A-401,674, KR 61639, OC-060062, OC-83839, OC-297962, MC52445, MC52453, ISIS 113715, and those disclosed in WO03/032916, WO03/032982, WO03/041729, WO03/055883, WO02/26707, WO02/26743, JP2002114768, and pharmaceutically acceptable salts and esters thereof;

sulfonylureas such as acetohexamide (e.g. Dymelor, Eli Lilly), carbutamide, chlorpropamide (e.g. Diabinese®, Pfizer), gliamilide (Pfizer), glibenclamide, gliclazide (e.g. Diamcron, Servier Canada Inc), glimepiride (e.g. disclosed in US437978, such as Amaryl™, Aventis), glipentide, glipizide (e.g. Glucotrol or Glucotrol XL Extended Release, Pfizer), gliquidone, glisolamide, glyburide, glibenclamide (e.g. Micronase or Glynase Prestab, Pharmacia & Upjohn and Diabeta, Aventis), tolazamide (e.g. Tolinase), and tolbutamide (e.g. Orinase), and pharmaceutically acceptable salts and esters thereof; meglitinides such as repaglinide (e.g. Pranidin®, Novo Nordisk), KAD1229 (PF/Kissei), and nateglinide (e.g. Starlix®, Novartis), and pharmaceutically acceptable salts and esters thereof;

alpha glucoside hydrolase inhibitors (or glucoside inhibitors) such as acarbose (e.g. Precose™, Bayer disclosed in U.S. Pat. No. 4,904,769), miglitol (such as GLYSET™, Pharmacia & Upjohn disclosed in U.S. Pat. No. 4,639,436), camiglibose (Methyl 6-deoxy-6-[(2R,3R,4R,5S)-3,4,5-trihydroxy-2-(hydroxymethyl)piperidino]-α-D-glucopyranoside, Marion Merrell Dow), voglibose (Takeda), adiposine, emiglitate, pradimicin-Q, salbostatin, CKD-711, MDL-25,637, MDL-73,945, and MOR 14, and the compounds disclosed in U.S. Pat. Nos. 4,062,950, 4,174,439, 4,254,256, 4,701,559, 4,639,436, 5,192,772, 4,634,765, 5,157,116, 5,504,078, 5,091,418, 5,217,877, US51091 and WO01/47528 (polyamines);

α-amylase inhibitors such as tendamistat, trestatin, and A1-3688, and the compounds disclosed in U.S. Pat. Nos. 4,451,455, 4,623,714, and 4,273,765;

insulin secreatagogues such as linogliride and A-4166 and pharmaceutically acceptable salts and esters thereof;

fatty acid oxidation inhibitors, such as clomoxir, and etomoxir, and pharmaceutically acceptable salts and esters thereof;

A2 antagonists, such as midaglizole, isaglidole, deriglidole, idazoxan, earoxan, and fluparoxan, and pharmaceutically acceptable salts and esters thereof;

insulin and related compounds (e.g. insulin mimetics) such as biota, LP-IOO, novarapid, insulin detemir, insulin lispro, insulin glargine, insulin zinc suspension (lente and ultralente), Lys-Pro insulin, GLP-I (1-36) amide, GLP-I (73-7) (insulintropin, disclosed in U.S. Pat. No. 5,614,492), LY-315902 (Lilly), GLP-I (7-36)-NH2), AL-401 (Autoimmune), certain compositions as disclosed in U.S. Pat. Nos. 4,579,730, 4,849,405, 4,963,526, 5,642,868, 5,763,396, 5,824,638, 5,843,866, 6,153,632, 6,191,105, and WO 85/05029, and primate, rodent, or rabbit insulin including biologically active variants thereof including allelic variants, more preferably human insulin available in recombinant form (sources of human insulin include pharmaceutically acceptable and sterile formulations such as those available from Eli Lilly (Indianapolis, Ind. 46285) as Humulin™ (human insulin rDNA origin), also see the THE PHYSICIAN'S DESK REFERENCE, 55.sup.th Ed. (2001) Medical Economics, Thomson Healthcare (disclosing other suitable human insulins);

non-thiazolidinediones such as JT-501 and farglitazar (GW-2570/GI-262579), and pharmaceutically acceptable salts and esters thereof;

PPARα/γ dual agonists such as AR-HO39242 (Aztrazeneca), GW-409544 (Glaxo-Wellcome), BVT-142, CLX-0940, GW-1536, GW-1929, GW-2433, KRP-297 (Kyorin Merck; 5-[(2,4-Dioxo thiazolidinyl)methyl]methoxy-N-[[4-(trifluoromethyl)phenyl]methyl]benzamide), L-796449, LR-90, MK-0767, SB 219994, muraglitazar, reglitazar (JTT-501) and those disclosed in WO99/16758, WO99/19313, WO99/20614, WO99/38850, WO00/23415, WO00/23417, WO00/23445, WO00/50414, WO01/00579, WO01/79150, WO02/062799, WO03/004458, WO03/016265, WO03/018010, WO03/033481, WO03/033450, WO03/033453, WO03/043985, WO 031053976 and pharmaceutically acceptable salts and esters thereof;

other insulin sensitizing drugs;

VPAC2 receptor agonists;

GLK modulators, such as those disclosed in WO03/015774;

retinoid modulators such as those disclosed in WO03/000249;

GSK 3β/GSK 3 inhibitors such as 4-[2-(2-bromophenyl)-4-(4-fluorophenyl-1H-imidazol-5-yl]pyridine and those compounds disclosed in WO03/024447, WO03/037869, WO03/037877, WO03/037891, WO03/068773, EP1295884, EP1295885, and the like;

glycogen phosphorylase (HGLPa) inhibitors such as CP-368,296, CP-316,819, BAYR3401, and compounds disclosed in WO01/94300, WO02/20530, WO03/037864, and pharmaceutically acceptable salts or esters thereof;

ATP consumption promotors such as those disclosed in WO03/007990;

TRB3 inhibitors;

vanilloid receptor ligands such as those disclosed in WO03/049702;

hypoglycemic agents such as those disclosed in WO03/015781 and WO03/040114;

glycogen synthase kinase 3 inhibitors such as those disclosed in WO03/035663;

agents such as those disclosed in WO99/51225, US20030134890, WO01/24786, and WO03/059870;

insulin-responsive DNA binding protein-1 (IRDBP-1) as disclosed in WO03/057827, and the like;

adenosine A2 antagonists such as those disclosed in WO03/035639, WO03/035640, and the like;

PPARδ agonists such as GW 501516, GW 590735, and compounds disclosed in JP10237049 and WO02/14291;

dipeptidyl peptidase IV (DP-IV) inhibitors, such as iso leucine thiazolidide, NVP-DPP728, P32/98, LAF 237, P3298, TSL225, valine pyrrolidide, TMC-2A/2B/2C, CD-26 inhibitors, FE999011, P9310/K364, VIP 0177, DPP4, SDZ 274-444, and the compounds disclosed in WO03/004498, WO03/004496, EP1258476, WO02/083128, WO02/062764, WO03/000250, WO03/002530, WO03/002531, WO03/002553, WO03/002593, WO03/000180, and WO03/000181;

GLP-I agonists such as exendin-3 and exendin-4 (including the 39 aa peptide synthetic exendin-4 called Exenatide®), and compounds disclosed in US2003087821 and NZ 504256, and pharmaceutically acceptable salts and esters thereof;

peptides including amlintide and Symlin® (pramlintide acetate);

glycokinase activators such as those disclosed in US2002103199 (fused heteroaromatic compounds) and WO02/48106 (isoindolin-1-one-substituted propionamide compounds); and other anti-diabetic agents such as cholestagel (Sankyo/Geltex), lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride), pancreatic cholesteryl hydrolase (pCEH) inhibitors (such as WAY-121898), omega 3 fatty acids, fish oil (which contains Omega 3 fatty acids (3-PUFA)), and ionenes such as disclosed in U.S. Pat. No. 4,027,009. Tests showing the efficacy of the therapy and the rationale for the combination therapy with an anti-diabetic agent are presented in US20040214811.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compounds taught herein can be suitably formulated into pharmaceutical compositions for administration to a subject. The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

The compounds and pharmaceutical compositions taught herein can be administered to a patient in a variety of forms depending on the selected route of administration, as will be understood by those skilled in the art.

The compounds and compositions of the present teachings can be administered by any available and effective delivery system including, but not limited to, orally, bucally, parenterally, by inhalation spray (oral or nasal), by topical application, by injection into the corpus cavernosum tissue, by transurethral drug delivery, vaginally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous injections, intramuscular injections, intrasternal injections, and infusion techniques. Parenteral also includes injection into the corpus cavernosum tissue, which can be conducted using any effective injection system including, but not limited to, conventional syringe-and-needle systems or needleless injection devices.

Solid dosage forms for oral administration can include capsules, tablets, effervescent tablets, chewable tablets, pills, powders, effervescent powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at body temperature, such that they will melt and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

For nasal administration, the compounds of the present teachings can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Topical administration, which is well known to one skilled in the art, involves the delivery of pharmaceutical agents via percutaneous passage of the drug into the systemic circulation of the patient. Topical administration includes vaginal administration, vulval administration, penile administration and rectal administration. Topical administration can also involve transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like.

Dosage forms for topical administration of the compounds and compositions of the present invention preferably include creams, sprays, lotions, gels, ointments, emulsions, coatings for condoms, liposomes, foams, and the like. Administration of the cream, spray, ointment, lotion, gel, emulsion, coating, liposome, or foam can be accompanied by the use of an applicator or by transurethral drug delivery using a syringe with or without a needle or penile insert or device, or by clitoral, vulval or vaginal delivery, and is within the skill of the art. Alternatively, the compositions may be contained within a vaginal ring, tampon, suppository, sponge, pillow, puff, or osmotic pump system; these platforms are useful solely for vaginal delivery. Typically a lubricant and/or a local anesthetic for desensitization can also be included in the formulation or provided for use as needed. Lubricants include, for example, K-Y jelly (available from Johnson & Johnson) or a lidocaine jelly, such as XYLOCAINE® 2% jelly (available from Astra Pharmaceutical Products). Local anesthetics include, for example, novocaine, procaine, tetracaine, benzocaine and the like.

Ointments are semisolid preparations that are typically based on petrolatum or other petroleum derivatives. The specific ointment base to be used, as will be appreciated by those skilled in the art, is one that will provide for optimum drug delivery. An ointment base should be inert, stable, nonirritating and nonsensitizing. Ointment bases may be grouped in four classes: oleaginous bases; emulsifiable bases; emulsion bases; and water-soluble bases. Oleaginous ointment bases include, for example, vegetable oils, fats obtained from animals, semisolid hydrocarbons obtained from petroleum, and the like. Emulsifiable ointment bases, also known as absorbent ointment bases, contain little or no welter and include, for example, hydroxystearin sulfate, anhydrous lanolin, hydrophilic petrolatum, and the like. Emulsion ointment bases are either water-in-oil (W/O) emulsions or oil-in-water (O/W) emulsions, and include, for example, cetyl alcohol, glyceryl monostearate, lanolin and stearic acid, and the like. In a particular embodiment, water-soluble ointment bases are preferred and are prepared from polyethylene glycols of varying molecular weight, and can be determined by standard techniques as described in Remington: The Science and Practice of Pharmacy.

Lotions are preparations that may be applied without friction, and are typically liquid or semiliquid preparations in which solid particles, including the active agent, are present in a water or alcohol base. Lotions are usually suspensions of solids, and in a particular embodiment, may comprise a liquid oily emulsion of the oil-in-water type. It is generally necessary that the insoluble matter in a lotion be finely divided. Lotions will typically contain suspending agents to produce better dispersions as well as compounds useful for localizing the active agent in contact with the skin, such as, for example, methylcellulose, sodium carboxymethyl-cellulose, and the like.

Emulsion formulations are generally formed from a dispersed phase (for example, a pharmacologically active agent), a dispersion medium and an emulsifying agent. If desired, emulsion stabilizers can be included in the formulation as well. A number of pharmaceutically useful emulsions are known in the art, including, for example, oil-in-water (o/w) formulations, water-in-oil (w/o) formulations and multiple emulsions such as w/o/w or o/w/o formulations. Emulsifying agents suitable for use in such formulations include, but are not limited to, TWEEN 60®, SPAN 80®, cetostearyl alcohol, myristyl alcohol, glyceryl monostearate, sodium lauryl sulfate, and the like.

Creams are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as, cetyl alcohol, stearyl alcohol, and the like; the aqueous phase usually, although not necessarily, exceeds the oil phase in volume, and generally contains a humectant. The emulsifier in a cream formulation is generally a nonionic, anionic, cationic or amphoteric surfactant.

For treatment of sexual dysfunction, the pharmaceutical formulation is administered to a subject via vaginal delivery, vulvar delivery, vulvar delivery, or urethral delivery. The amount of active agent administered is at least the minimum necessary to treat the dysfunction, e.g., excitement stage dysfunctions such as touch sensation impairment, loss of clitoral sensation, vaginal dryness, urinary incontinence and concomitant dyspareunia.

The term "vaginal delivery" is used herein to mean direct administration of a pharmaceutical composition to the vagina of the individual undergoing treatment. Generally, "vaginal delivery" of a pharmaceutical composition involves administration to the distal several centimeters of the vagina.

The term "vulvar delivery" or "vulvar administration" is used herein to refer to application of a pharmaceutical formulation to the vulvar area of an individual undergoing treatment. The term is intended to encompass application to the clitoris as well as the surrounding vulvar area. The terms "vulvar delivery" and "clitoral delivery" are used interchangeably herein and are both intended to refer to administration to the vulvar area of the individual undergoing treatment.

The term "urethral delivery" (sometimes referred to as "intraurethral" or "transurethral" delivery) is used herein to mean direct administration of a pharmaceutical composition to the urethra of the individual undergoing treatment. Generally, "urethral" delivery of a pharmaceutical composition involves administration to the distal portion of the urethra.

Transurethral administration of the pharmaceutical compositions disclosed herein can be carried out in a number of different ways. For example, the pharmaceutical compositions can be introduced into the urethra from a flexible tube, squeeze bottle, pump or aerosol spray. The pharmaceutical compositions may also be contained in coatings, pellets or suppositories which are absorbed, melted or bioeroded in the urethra. The drug formulation may be included as a coating on the exterior surface of a urethral insert.

Compounds described herein may be prepared using the reaction routes and syntheses described below, employing the techniques available in the art using starting materials that are readily available.

The invention is illustrated by the following examples which are not intended to be limiting in any way.

EXEMPLIFICATION

Example 1

Synthesis of (Z)-1-((2-(4-(4-chlorobenzoyl)phenoxy)-2-methylpropanoyloxy)methoxy)-3-(2-hydroxyethyl)-3-methyltriaz-1-ene 2-oxide 6

6

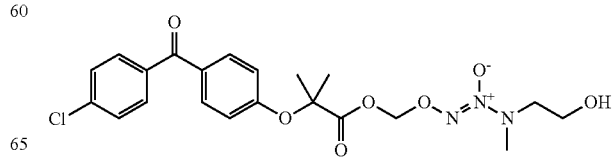

A. Synthesis of chloromethyl 2-(4-(4-chlorobenzoyl)phenoxy)-2-methylpropanoate 1

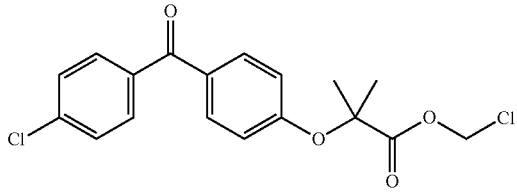

1

A mixture of 2-(4-(4-chlorobenzoyl)phenoxy)-2-methylpropanoic acid (10.0 g, 31.4 mmol), sodium bicarbonate (13.2 g, 47.1 mmol, 1.5 eq) and tetrabutylammonium hydrogensulfate (2.1 g, 6.3 mmol, 0.2 eq) in water (150 mL) was stirred at room temperature for 15 min. Dichloromethane (150 mL) was added and the mixture was cooled in ice. Chloromethyl sulfochloridate (4.2 mL, 47.1 mmol, 1.5 eq) was added and the mixture was stirred overnight at room temperature. The layers were separated, the organic phase was washed with water (50 mL) and brine, then dried over sodium sulfate. The drying agent was filtered off and the solution was concentrated by rotary evaporation to leave a thick oil. Hexane (50 mL) and seeds were added and rotary evaporation was continued at room temperature to leave chloromethyl 2-(4-(4-chlorobenzoyl)phenoxy)-2-methylpropanoate 1 as a white solid (11.6 g, 101% yield). $^1$H-NMR (CDCl$_3$) δ 7.73 (d, 2 H), 7.70 (d, 2 H), 7.44 (d, 2 H), 6.87 (d, 2 H), 5.77, (s, 2 H), 1.70 (s, 6 H) ppm.

B. Synthesis of iodomethyl 2-(4-(4-chlorobenzoyl)phenoxy)-2-methylpropanoate 2

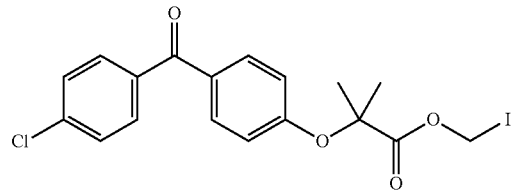

2

Chloromethyl 2-(4-(4-chlorobenzoyl)phenoxy)-2-methylpropanoate 1 (3.0 g, 8.2 mmol) was dissolved in acetone (50 mL) at room temperature. Sodium iodide (2.4 g, 16.3 mmol, 2 eq) was added and the clear solution was stirred 10 min at room temperature, then heated to 50° C. for 6 hr. The mixture was cooled to room temperature, diluted with ethyl acetate (200 mL) and filtered. The filtrate was washed with water (3×10 mL) and brine then dried over sodium sulfate. The drying agent was filtered off and the solution was concentrated by rotary evaporation to leave iodomethyl 2-(4-(4-chlorobenzoyl)phenoxy)-2-methylpropanoate 2 as a thick, yellow oil (3.7 g, 99% yield) that was used directly in the next reaction without further purification. $^1$H-NMR (CDCl$_3$) δ 7.74 (d, 2 H), 7.71 (d, 2 H), 7.45 (d, 2 H), 6.85 (d, 2 H), 5.97, (s, 2 H), 1.67 (s, 6 H) ppm.

C. Synthesis of the Sodium NONOate Salt of 2-(methylamino)ethanol 3

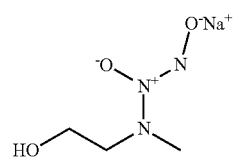

3

A solution of 2-(methylamino)ethanol (3.0 g, 39.9 mmol) in ether (20 mL) and tetrahydrofuran (20 mL) was prepared at room temperature in a 200 mL pressure vessel (Ace Glass). A solution of sodium methoxide in methanol (25 wt %, 11.0 mL, 47.9 mmol, 1.2 eq) was added and the solution was stirred 15 min at room temperature. The vessel was sealed, purged with nitric oxide gas (2×20 psi), then the pressure of NO was adjusted to 30 psi and stirring was continued overnight at room temperature. The vessel was opened, flushed for 5 min with N2, then diluted with ether (100 mL) and filtered. The filter cake was washed with ether (3×50 mL), then dried under high vacuum to leave the sodium NONOate salt of 2-(methylamino)ethanol 3 as a white solid (4.7 g, 76% yield). $^1$H-NMR (D$_2$O) δ 4.65 (s, 1 H), 3.37 (t, 2 H), 2.89 (t, 2 H), 2.58 (s, 3 H) ppm.

D. Synthesis of (Z)-1-((2-(4-(4-chlorobenzoyl)phenoxy)-2-methylpropanoyloxy)methoxy)-3-(2-hydroxyethyl)-3-methyltriaz-1-ene 2-oxide 6

A suspension of the sodium NONOate salt of (2-methylamino)ethanol 3 (1.1 g, 7.1 mmol, 1.3 eq) was prepared in dimethylformamide (10 mL) and cooled in ice. A solution of iodomethyl 2-(4-(4-chlorobenzoyl)phenoxy)-2-methylpropanoate 2 (2.5 g, 5.4 mmol, 1 eq) in dimethylformamide (5 mL) was added to the stirred suspension over 4 min, then the mixture was stirred at room temperature for 1 hr. The dimethylformamide was removed under vacuum at 40° C., then the residue was taken up in ethyl acetate (100 mL) and washed with water (3×30 mL) and brine then dried over sodium sulfate. The drying agent was filtered off and the solution was concentrated by rotary evaporation. Purification was effected by liquid chromatography over silica gel, eluting with a gradient mixture of hexane/ethyl acetate. The product (Z)-1-((2-(4-(4-chlorobenzoyl)phenoxy)-2-methylpropanoyloxy)methoxy)-3-(2-hydroxyethyl)-3-methyltriaz-1-ene 2-oxide 6 was obtained as a thick, colorless gum that solidified on standing (0.64 g, 25% yield). $^1$H-NMR (CDCl$_3$) δ 7.71 (d, 2 H), 7.70 (d, 2 H), 7.44 (d, 2 H), 6.83 (d, 2 H), 5.84, (s, 2H), 3.68 (t, 2 H), 3.41 (t, 2 H), 2.90 (s, 3 H), 1.69 (s, 6 H) ppm.

Example 2

Synthesis of (Z)-1-((2-(4-(4-chlorobenzoyl)phenoxy)-2-methylpropanoyloxy)methoxy)-3-(4-hydroxybutyl)-3-methyltriaz-1-ene 2-oxide 7

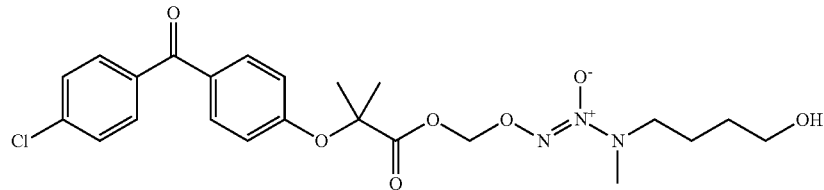

A. Synthesis of the Sodium NONOate Salt of 4-(methylamino)-n-butanol 4

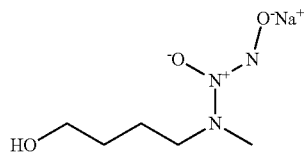

A solution of 2-(methylamino)ethanol (2.9 g, 28.1 mmol) in ether (30 mL) and tetrahydrofuran (30 mL) was prepared at room temperature in a 200 mL pressure vessel (Ace Glass). A solution of sodium methoxide in methanol (25 wt %, 7.7 mL, 33.7 mmol, 1.2 eq) was added and the solution was stirred 15 min at room temperature. The vessel was sealed, purged with nitric oxide gas (2×20 psi), then the pressure of NO was adjusted to 30 psi and stirring was continued overnight at room temperature. The vessel was opened, flushed for 5 min with N2 for 5 min with $N_2$, then ether (60 mL) was added. A thick gum had precipitated on the sides of the vessel. The solvent was decanted off and the gummy residue was rinsed with ether (2×30 mL), tetrahydrofuran (30 mL), then transferred to a roundbottom flask with methanol (20 mL) and concentrated by rotary evaporation and finally dried at high vacuum overnight to leave the sodium NONOate salt of 4-(methylamino)-n-butanol 3 as a light yellow solid (3.1 g, 59% yield).

$^1$H-NMR ($D_2O$) δ 4.65 (s, 1 H), 3.42 (t, 2 H), 2.76 (t, 2 H), 2.56 (s, 3 H), 1.41 (t, 2 H), 1.23 (t, 2 H) ppm.

B. Synthesis of (Z)-1-((2-(4-(4-chlorobenzoyl)phenoxy)-2-methylpropanoyloxy)methoxy)-3-(4-hydroxybutyl)-3-methyltriaz-1-ene 2-oxide 7

A suspension of the sodium NONOate salt of (2-methylamino)-n-butanol 4 (1.3 g, 7.1 mmol, 1.3 eq) was prepared in dimethylformamide (40 mL) and cooled in ice. A solution of iodomethyl 2-(4-(4-chlorobenzoyl)phenoxy)-2-methylpropanoate 2 (2.5 g, 5.4 mmol, 1 eq) in dimethylformamide (10 mL) was added to the stirred suspension over 8 min, then the mixture was stirred at room temperature for 1.5 hr. The reaction mixture was diluted with ethyl acetate (400 mL) and washed with water (6×20 mL), brine then dried over sodium sulfate. The drying agent was filtered off and the solution was concentrated by rotary evaporation. Purification was effected by liquid chromatography over silica gel, eluting with a gradient mixture of hexane/ethyl acetate. The product ((Z)-1-((2-(4-(4-chlorobenzoyl)phenoxy)-2-methylpropanoyloxy)methoxy)-3-(4-hydroxybutyl)-3-methyltriaz-1-ene 2-oxide 7 was obtained as a light yellow oil (0.23 g, 8% yield). $^1$H-NMR (CDCl$_3$) δ 7.72 (d, 4 H), 7.45 (d, 2 H), 6.85 (d, 2 H), 5.86, (s, 2 H), 3.62 (t, 2 H), 3.27 (t, 2 H), 2.85 (s, 3 H), 1.69 (s, 6 H), 1.50-1.55 (m, 4 H) ppm.

Example 3

Synthesis of (S,Z)-2-((2-(4-(4-chlorobenzoyl)phenoxy)-2-methylpropanoyloxy)methoxy)-1-(2-(hydroxymethyl)pyrrolidin-1-yl)diazene oxide 8

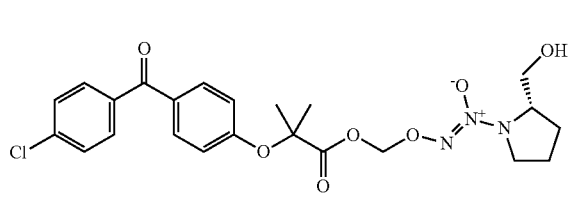

A. Synthesis of the Sodium NONOate Salt of L-prolinol 5

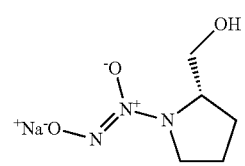

A solution of L-prolinol (5.0 g, 49.4 mmol) in ether (40 mL) and tetrahydrofuran (40 mL) was prepared at room temperature in a 250 mL pressure vessel (Ace Glass). A solution of sodium methoxide in methanol (25 wt %, 13.6 mL, 59.3 mmol, 1.2 eq) was added and the solution was stirred 10 min at room temperature. The vessel was sealed, purged with nitric oxide gas (2×20 psi), then the pressure of NO was adjusted to 25 psi and stirring was continued overnight at room temperature. The vessel was opened, flushed for 5 min with N2, then diluted with ether (80 mL) and filtered. The filter cake was washed with ether (2×60 mL), then dried under high vacuum to leave the sodium NONOate salt of L-prolinol 5 as a white solid (7.6 g, 83% yield). $^1$H-NMR ($D_2O$) δ 4.65

(s, 1 H), 3.30-3.45 (m, 3 H), 3.19 (dd, 1 H), 1.85-1.95 (m, 1H), 1.75-1.85 (m, 1H), 1.65-1.75 (m, 1H), 1.45-1.55 (m, 1H), ppm.

B. Synthesis of (S,Z)-2-((2-(4-(4-chlorobenzoyl) phenoxy)-2-methylpropanoyloxy) methoxy)-1-(2-(hydroxymethyl)pyrrolidin-1-yl)diazene oxide 8

A suspension of the sodium NONOate salt of L-prolinol 5 (0.65 g, 3.6 mmol, 1.3 eq) was prepared in dimethylformamide (6 mL) and cooled in ice. A solution of iodomethyl 2-(4-(4-chlorobenzoyl)phenoxy)-2-methylpropanoate 2 (1.26 g, 2.8 mmol, 1 eq) in dimethylformamide (4 mL) was added to the stirred suspension over 4 min, then the mixture was stirred at room temperature for 1 hr. The dimethylformamide was removed under vacuum at 40° C., then the residue was taken up in ethyl acetate (100 mL) and washed with water (3×30 mL) and brine then dried over sodium sulfate. The drying agent was filtered off and the solution was concentrated by rotary evaporation. Purification was effected by liquid chromatography over silica gel, eluting with a gradient mixture of hexane/ethyl acetate. The product (S,Z)-2-((2-(4-(4-chlorobenzoyl)phenoxy)-2-methylpropanoyloxy)methoxy)-1-(2-(hydroxymethyl)pyrrolidin-1-yl)diazene oxide 8 was obtained as a crunchy, light yellow foam (0.46 g, 32% yield). $^1$H-NMR (CDCl$_3$) δ 7.72 (d, 2 H), 7.71 (d, 2 H), 7.45 (d, 2 H), 6.85 (d, 2 H), 5.86, (d, 1H), 5.79, (d, 1 H), 3.90-4.00 (m, 1 H), 3.65-3.70 (m, 1 H), 3.50-3.60 (m, 1H), 3.40-3.50 (m, 1 H), 3.30-3.40 (m, 1H), 2.78 (t, 1 H), 1.80-2.00 (m, 4 H), 1.70 (s, 6 H) ppm.

Example 4

Pharmacokinetics of Fenofibrate and Nitric Oxide Upon Oral Dosing in Male Rats 15 male SD (Sprague Dawley) rats were allowed to acclimate for at least 3 days. Fenofibrate, compounds 6, 7, and 8 were administered via oral gavage at molar equivalent doses of 24.8, 32, 34, 33.8 mg/kg, respectively. Animals were fasted overnight and had their food replaced 4 hours after dosing. Compounds were formulated in 300 µL of 100% PEG400. Animals were euthanized under $CO_2$ at the 24 hr time point. Plasma samples were taken for analytical determination of fenofibric acid from compounds in vacutainers containing sodium fluoride. Serum samples were taken for nitric oxide level determination in BD serum collection tubes.

Fenofibric acid was extracted from the plasma using an acetonitrile protein precipitation method. Samples were run on a Waters Aquity TQD LC-MS/MS and analyzed using the MassLynx software. Nitric Oxide levels were measured in serum using a Nitrate/Nitrite Colorimetric Assay Kit from Caymen Chemicals.

Upon oral dosing with compounds 6, 7, and 8, a similar fenofibric acid PK profile was demonstrated compared to dosing with fenofibric acid. See FIG. 1. There is no increase in nitric oxide in the plasma upon dosing with fenofibrate. However, upon dosing with compounds 6, 7, or 8, a robust increase in nitric oxide levels is seen. See FIG. 2.

Example 5

Biological Activity Measurement by the Thoracic Aortic Rings Assay

Thoracic aortic rings were dissected from anesthetized (isoflurane) male Sprague-Dawley rats weighing 275-299 g. Tissues were immediately transferred to ice-cold Krebs-Henseleit solution, which had been aerated with 95% $O_2$ and 5% $CO_2$ for 30 minutes. Following removal of connective tissue, aortic sections were cut into 4 rings (~2 mm each) and suspended on 2 L-shaped hooks, with one hook fixed at the bottom of the tissue bath (Schuler Organ Bath, Harvard Apparatus) and the other connected to a force transducer (F30 Force Transducer, Harvard Apparatus). Baths contained Krebs Henseleit solution (10 mL) heated to 37° C. and aerated with 95% $O_2$ and 5% $CO_2$. Rings were brought to an initial tension of 0.3-0.5 g and gradually raised to a resting tension of 1.0 g over 60 minutes. Rings were rinsed with Krebs Henseleit solution (heated to 37° C. and aerated with 95% 02 and 5% $CO_2$) at 15 minute intervals until a stable baseline was obtained. Rings were considered to be stable after a resting tension of 1.0 g was maintained (for approximately 10 minutes) without need for adjustment. Rings were then contracted with 100 ng/mL phenylephrine by adding 100 uL of a 10 µg/mL phenylephrine stock solution. Tissues achieving a stable contraction were then treated in a cumulative, dose dependent manner with test compounds prepared in dimethylsulfoxide (DMSO). In some cases, tissues were rinsed three times over a 5 minute period with Krebs-Heinseleit's solution (heated to 37° C. and aerated with 95% $O_2$ and 5% $CO_2$), allowed to stabilize at baseline, and then used for characterization of other test articles or DMSO effects. All data were collected using the HSE-ACAD software provided by Harvard Apparatus. Percent relaxation effects were calculated in Microsoft Excel using the recorded tension value of 100 ng/mL phenylephrine treatment as 0% inhibition and treatment with 100 µM 3-isobutyl-1-methylxanthine as 100% inhibition. $EC_{50}$ values were calculated from concentration-response curves generated with GraphPad Prism Software. As an alternative thoracic aortic rings assay percent relaxation effects were calculated in Microsoft Excel using the recorded tension value of 100 ng/mL phenylephrine treatment as 0% inhibition and, after washing the tissue with buffer, the original resting tension of the tissue was used as 100% inhibition.

Compounds 6 and 8 were tested in the rat aortic ring assay and were determined to posses potent vasorelaxant properties in the nM range. A control compound, ISDN, was active in this assay as a vasorelaxant in the micromolar range. See FIG. 3.

Example 6

Rat High Fat, High Cholesterol Diet Model

Compounds were tested for effects on cholesterol and lipid profiles in a rat high fat diet model for example as described in Ghibaudi et al. (2002) Obes Res 10:956-63, Ricci and Levin (2003) Am J Physiol Regul Integr Comp Physiol 285: R610-8, and Gao et al. (2002) 936:87-90. Alternatively, animals were fed either a normal diet or a chow supplemented with added fat and/or cholesterol as described in Krause et al (1994) Pharm Res Vol 29, No. 4, Nishina (1993) J of Lipid Res vol 43. and Gajda et al. (2007) Animal Lab News. Based on the specific chows used in these reports, animals were fed a diet consisting of 40% fat, 1% cholesterol, and 0.5% cholic acid (catalog #D01061201, Research Diets, New Brunswick, N.J. 08901).

After at least a week on this diet, animals (6-8/group) are dosed once daily perorally with 500 uL test compounds in PEG 400. Groups are dosed for at least one week before whole blood samples are taken for analysis. Blood serum is analyzed using Vertical Auto Profile (VAP; Atherotech, Inc., Birmingham, Ala.) analysis similar to as described in Kulkarni (2006) Clin Lab Med 26:787-802.

Fenofibrate (Sigma—Cat# F6020-5G, Lot#017K1401) was tested in this assay at 2.2, 7.3 and 22 mg/kg which were equimolar equivalents (for the fenofibric acid moiety) of Compound 8 dosed at 3, 10 and 30 mg/kg. In these experiments animals (n=6 per group) were fed a high fat high cholesterol chow (HFHC; 40% fat, 1% cholesterol, 0.5% cholic acid) diet for one week before test compound administration. Animals received either vehicle only (PEG 400) or test compound (compound 8 at 3, 10 or 30 mg/kg or fenofibrate at 2.2, 7.3 or 22 mg/kg) for seven days before whole blood samples were taken for analysis.

The test results show compound 8 was associated with dose related increases in HDL and decreases in very low-density lipoprotein (VLDL) cholesterol. These effects of compound 8 were similar to that seen with equimolar doses of Fenofibrate (increases in HDL and decreases in VLDL) when tested in this assay. Graphical depictions showing the VLDL and HDL analyses for compounds 8 and Fenofibrate are shown in FIGS. 4 and 5 respectively.

Example 7

Rat Normotensive Blood Pressure Model 36 male SD rats were allowed to acclimate for at least 3 days. After conditioning the rats were arterially cannulated and assigned to 4 treatment groups, with the goal of achieving n=6/group.

After the acclimation period, the rats were briefly anesthetized with inhaled isoflurane and implanted a small bore femoral artery cannula to permit CV monitoring under conscious unrestrained conditions as conducted in prior studies. 18 rats were cannulated per day on 2 consecutive days and allowed 2 days of post-operative recovery prior to CV testing. 12 rats per day were monitored for each of 2 consecutive daily test sessions.

On the morning of the test sessions, the rats were placed in individual bell jars and their femoral artery cannulas were attached to pressure transducers. CV monitoring consisted of continuously recording mean arterial pressure (MAP) and spot checking heart rate (HR; every 5 to 7 minutes) prior to and for 6 hours after a single oral treatment as in previous studies.

Also on the morning of testing, 4 oral treatments in 500 μl of 100% PEG 400 were formulated. The rats were allowed about 1 hour of equilibration prior to dosing. Once suitably equilibrated, each rat was dosed with an oral vehicle or a drug, delivered by standard gavage. The CV recording was continued over the 6-hour post-treatment interval, occasional small flushes of heparinized saline (~0.1 mL; 20 units/mL) were administered into their arterial catheters in order to maintain recording fidelity.

At the conclusion of the 6-hour CV monitoring interval, a terminal ~0.6 mL arterial blood sample was taken and the serum or plasma was processed.

In this assay, Compounds 6, 7, and 8 were tested and show lowering blood pressure in a normotensive rat model. See FIG. 6.

Example 8

Rat L-NAME Induced Hypertension Blood Pressure Model

L-NAME induced hypertension model was carried out at Pharmoptima. Based on the rats' projected average daily water intake, the NO synthase inhibitor L-NAME, L-NG-nitroarginine methyl ester, which induces hypertension, were dissolved in their drinking water so that the rats self-administered tested compounds for 2 weeks prior to study at the targeted daily L-NAME dosage. The rats' L-NAME/water solution was reformulated every other day to insure potency.

After 2 weeks of oral L-NAME preconditioning, the rats were anesthetized with inhaled isoflurane (3-4% in oxygen) and implanted a small bore femoral artery catheter to permit cardiovascular (CV) monitoring under conscious unrestrained conditions. A total of 36 rats (18 rats/day on two consecutive days) were prepared. The catheters were sealed with sodium heparin to maintain patency.

Allow 2 days of post-operative recovery prior to study, allowing full access to food and water (containing dissolved L-NAME) water.

On the study treatment day, 15 rats (n=6×5 treatments) were set up in bell jars under routine non-fasted conditions. Start recording mean arterial pressure (MAP) and heart rate (HR) from this first set of cannulated rats as per previous studies conducted by PharmOptima. Once stable, the rats were dosed by oral gavage. CV data were recorded from the rats over the ensuing 6 hours. 3 arterial blood samples were taken per rat and the harvested plasma samples were frozen.

In this assay, compound 8 was tested at 10, 30, and 60 mg/kg and lowered blood pressure in an L-NAME model of hypertension in a dose responsive manner. In contrast, Fenofibrate did not lower blood pressure in the same model. A control compound, ISDN (isosorbide dinitrate), had a moderate blood pressure lowering effect. See FIGS. 7 and 8.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by the structure of Formula I:

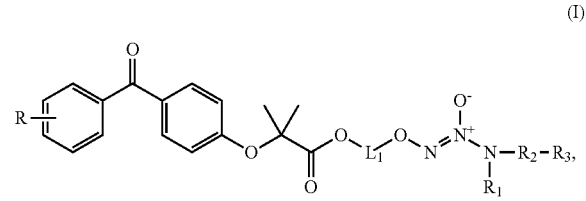

or a pharmaceutically acceptable salt thereof, wherein:
R is selected from halogen, —CN, —NO$_2$, C1-C4 alkyl, C1-C4 haloalkyl, C1-C4 alkoxy, C1-C4 haloalkoxy, —C(=O)OR$^a$, and —OC(=O)R$^a$;
R$_1$ is H or optionally substituted C1-C4 alkyl;
R$_2$ is optionally substituted C1-C6 alkylene; or
R$_1$ and R$_2$, together with the nitrogen to which they are attached, form a 3-8 membered heterocyclic ring, referred as ring A, wherein the ring is optionally substituted by R$_3$;
R$_3$ is —H, —OH, —CO$_2$R$^a$, halogen, —NR$^b$R$^c$, —CN, C1-C4 alkyl, C1-C4 haloalkyl, C1-C4 hydroxyalkyl, C1-C4 alkoxy, C1-C4 haloalkoxy, or (C1-C4)alkoxy(C1-C4)alkyl;
L$_1$ is C1-C6 alkylene;
each R$^a$, independently, is —H or C1-C4 alkyl; and $R^b$ and $R^c$ are each independently selected from —H, C1-C4 alkyl, C1-C4 haloalkyl, hydroxy(C1-C4)alkyl, and (C1-C4)alkoxy(C1-C4)alkyl.

2. The compound of claim 1, wherein the compound is represented by the structure of Formula II:

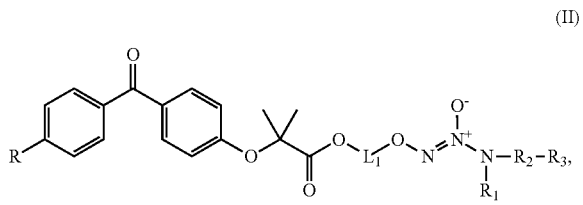

or a pharmaceutically acceptable salt thereof.

3. The compound of claim 2, wherein R is selected from halogen, —CN, C1-C4 alkyl, and C1-C4 haloalkyl.

4. The compound of claim 3, wherein the compound is represented by the structure of Formula IIa:

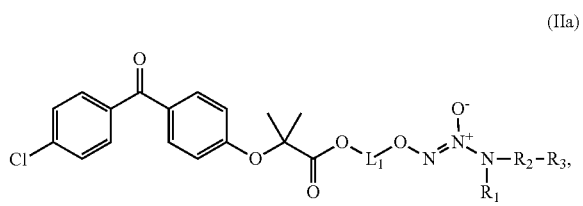

or a pharmaceutically acceptable salt thereof.

5. The compound of claim 4, wherein
$R_1$ is H or C1-C4 alkyl, optionally substituted with 1 to 3 substituents independently selected from halogen, —NR$^b$R$^c$, hydroxyl, and C1-C4 alkoxy; and
$R_2$ is C1-C6 alkylene, optionally substituted with 1 to 3 substituents independently selected from halogen, —NR$^b$R$^c$, hydroxyl, and C1-C4 alkoxy.

6. The compound of claim 5, wherein
$R_1$ is H or C1-C4 alkyl;
$R_2$ is C1-C6 alkylene;
$R_3$ is —H, —OH, C1-C4 hydroxyalkyl, or C1-C4 alkoxy; and
$L_1$ is C1-C3 alkylene.

7. The compound of claim 6, wherein
$R_1$ is —H or -methyl;
$R_3$ is —H, OH, or CH$_2$OH; and
$L_1$ is —CH$_2$—.

8. The compound of claim 3, wherein the compound is represented by the structure of Formula IIb:

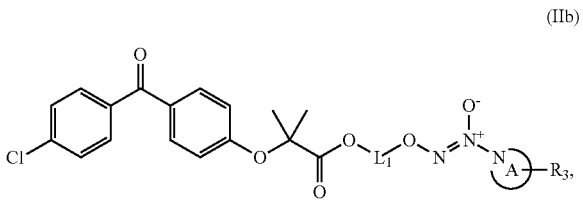

or a pharmaceutically acceptable salt thereof, wherein:

ring A is a 3-8 membered heterocyclic ring, optionally substituted with a group represented by $R_3$.

9. The compound of claim 8, wherein ring A is selected from aziridinyl, diazirinyl, diaziridinyl, azetidinyl, 1,2-diazetidinyl, morpholinyl, thiomorpholinyl, pyrrolidinonyl, pyrrolidinyl, piperidinyl, piperazinyl, hydantoinyl, valerolactamyl, dihydroimidazole, dihydropyridinyl, dihydropyrimidinyl, tetrahydroimidazole, tetrahydropyridinyl, tetrahydropyrimidinyl, azepinyl, diazepinyl, azepanyl, diazepanyl, imidazolyl, isoxazolyl, oxadiazolyl, oxazolyl, pyrazolyl, pyrrolyl, pyridyl, pyrimidinyl, pyridazinyl, thiazolyl, isothiazolyl, triazolyl, and tetrazolyl.

10. The compound of claim 9, wherein ring A is selected from aziridinyl, azetidinyl, pyrrolidinyl, piperidinyl, and morpholinyl.

11. The compound of claim 10, wherein
ring A is pyrrolidinyl;
$R_3$ is —H, —OH, C1-C4 hydroxyalkyl, —CO$_2$R$^a$, or C1-C4 alkoxy; and
$L_1$ is C1-C3 alkylene.

12. The compound of claim 11, wherein $R_3$ is —H, —CH$_2$OH, or —OH and $L_1$ is —CH$_2$—.

13. The compound of claim 1, wherein the compound is

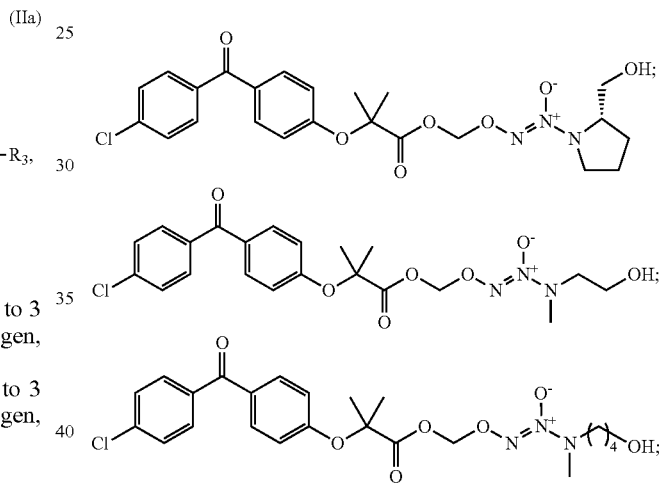

or a pharmaceutically acceptable salt thereof.

14. A pharmaceutical composition comprising a compound of claim 1 and a pharmaceutically acceptable carrier or diluent.

15. A method for increasing NO levels in a subject in need thereof, the method comprising administering to a subject in need thereof a therapeutically effective amount of the compound according to claim 1.

16. The method of claim 15, wherein the subject is in need of treatment for a disease or disorder selected from lipid related disorder, hypertension, fungal infection, female sexual dysfunction, erectile dysfunction, thrombosis, or inhibiting platelet aggregation in a subject in need thereof.

17. The method of claim 15, wherein the subject is in need of treatment for a disease or disorder selected from diabetes, elevated fasting plasma glucose, insulin resistance, elevated glycosylated hemoglobin levels, diabetic retinopathy, proliferative or non-proliferative retinopathy, albuminuria, microalbuminuria, nephropathy, kidney failure, neuropathy, and foot ulcers.

* * * * *